(12) United States Patent
Tsao

(10) Patent No.: US 10,759,860 B2
(45) Date of Patent: Sep. 1, 2020

(54) ANTI-EGFR ANTIBODY AND USES OF SAME

(71) Applicant: SYNERMORE BIOLOGICS CO., LTD., Taipei (TW)

(72) Inventor: Eric Tsao, Potomac, MD (US)

(73) Assignee: Synermore Biologics Co., Ltd., Taipei (TW)

( * ) Notice: Subject to any disclaimer, the term of this patent is extended or adjusted under 35 U.S.C. 154(b) by 0 days.

(21) Appl. No.: 15/128,824

(22) PCT Filed: Sep. 15, 2015

(86) PCT No.: PCT/US2015/050131
§ 371 (c)(1),
(2) Date: Sep. 23, 2016

(87) PCT Pub. No.: WO2016/044234
PCT Pub. Date: Mar. 24, 2016

(65) Prior Publication Data
US 2017/0267765 A1   Sep. 21, 2017

Related U.S. Application Data

(60) Provisional application No. 62/051,126, filed on Sep. 16, 2014.

(51) Int. Cl.
*C07K 16/28*  (2006.01)
*C07K 16/30*  (2006.01)
(Continued)

(52) U.S. Cl.
CPC ...... *C07K 16/2863* (2013.01); *A61K 39/3955* (2013.01); *A61K 45/06* (2013.01);
(Continued)

(58) Field of Classification Search
None
See application file for complete search history.

(56) References Cited

U.S. PATENT DOCUMENTS 8,450,068 B2 *  5/2013  Platts-Mills ....... C07K 16/4291
                                               424/805
8,580,524 B2 * 11/2013  Banik ................. G01N 33/6854
                                                435/7.1
(Continued)

FOREIGN PATENT DOCUMENTS

CN        105399830        3/2016
WO     WO-2007/147001      12/2007
(Continued)

OTHER PUBLICATIONS

Chung, et al., Cetuximab-induced anaphylaxis and IgE specific for galactose-.alpha.-1,3-galactose, N. Engl. J. Med. 358:1109-1117, 2008.*

(Continued)

Primary Examiner — Claire Kaufman
(74) Attorney, Agent, or Firm — Foley & Lardner LLP

(57) ABSTRACT

This disclosure relates generally to an EGFR antibody and its therapeutic effects on tumor inhibition in vitro and in vivo, alone or in combination with various chemotherapeutic agents. In particular, the present disclosure relates to methods for the treatment of cancer, comprising administering an EGFR antibody, alone or in combination with a chemotherapeutic agent.

18 Claims, 21 Drawing Sheets

Specification includes a Sequence Listing.

(51) Int. Cl.
| | |
|---|---|
| *C12N 5/16* | (2006.01) |
| *C12N 15/09* | (2006.01) |
| *A61K 39/395* | (2006.01) |
| *A61K 47/68* | (2017.01) |
| *A61K 45/06* | (2006.01) |
| *C12P 21/00* | (2006.01) |
| *G01N 33/50* | (2006.01) |
| *G01N 33/68* | (2006.01) |
| *C07K 14/71* | (2006.01) |
| *A61K 39/00* | (2006.01) |

(52) U.S. Cl.
CPC .......... *A61K 47/6849* (2017.08); *C07K 16/30* (2013.01); *C12P 21/005* (2013.01); *G01N 33/5088* (2013.01); *G01N 33/6854* (2013.01); *A61K 2039/505* (2013.01); *A61K 2039/545* (2013.01); *C07K 2317/14* (2013.01); *C07K 2317/24* (2013.01); *C07K 2317/41* (2013.01); *C07K 2317/732* (2013.01); *C07K 2317/76* (2013.01); *C07K 2317/92* (2013.01); *C07K 2317/94* (2013.01); *C07K 2319/03* (2013.01); *C07K 2319/033* (2013.01)

(56) References Cited

U.S. PATENT DOCUMENTS

| | | | |
|---|---|---|---|
| 9,359,439 B2 * | 6/2016 | Goletz | C07K 16/00 |
| 9,493,568 B2 * | 11/2016 | Reilly | A61K 47/48561 |
| 2010/0120058 A1 | 5/2010 | Platts-Mills et al. | |
| 2014/0178415 A1 | 6/2014 | Li et al. | |
| 2015/0071923 A1 * | 3/2015 | Wei | C07K 16/30 |

FOREIGN PATENT DOCUMENTS

| | | |
|---|---|---|
| WO | WO-2008/135259 | 11/2008 |
| WO | WO-2011/116387 | 9/2011 |
| WO | WO-2013/134743 | 9/2013 |
| WO | WO-2014/066606 | 5/2014 |
| WO | WO-2014/100740 | 6/2014 |

OTHER PUBLICATIONS

Raju, T.S. Glycosylation variations with expression systems and their impact on biological activity of therapeutic immunoglobulins, Bioprocess Intl, 1:42-53, Apr. 2003.*

Chamberlain, P., Multidisciplinary approach to evaluating immunogenicity of biosimilars: lessons learnt and open questions based on 10 years' experience of the European Union regulatory pathway, [online], retrieved Mar. 1, 2018 from URL:<https://doi.org/10.2147/BS.S50012>, Dovepress, 2014(4):23, 25 Jun. 2014.*

Ebbers et al., Interchaneability. An insurmaountable fifth hurdle?, Retrieved online Mar. 1, 2018 from URL:<http://gabi-journal.net/interchangeability-an-insurmountable-fifth-hurdle.html>, Genetics Biosimilar Initiative J.(GaBi J.), 3(2):88-93, Apr. 16, 2014.*

Ayoub et al.,Correct primary structure assessment and extensive glyco-profiling of cetuximab by a combination of intact, middle-up, middle-down and bottom-up ESI and MALDI mass spectrometry, mAbs, 5(5):699-710, and supplemental materail, Jun. 2013.*

International Preliminary Report on patentability issued on PCT/US2015/050131, dated Mar. 21, 2017.

Office Action issued on Canadian Application 2,944,085, dated Mar. 9, 2017.

Office Action issued on Japanese Application 2016-560759, dated Mar. 13, 2017 English Translation only.

Notice of Preliminary Rejection issued on Korean Application 10-2016-7027348, dated Nov. 24, 2017, English translation only.

Beck, Alain, "Biosimilar, biobetter and next generation therapeutic antibodies," Landes Biosciences, Mar./Apr. 2011, vol. 3, No. 2, pp. 107-110.

Extended Search Report issued on EP Appl. 15841946.5, dated Jul. 25, 2017.

Wang et al., "Phase 1 study of anti-epidermal growth factor receptor monoclonal antibody in patients with solid tumors," Landes Bioscience, vol. 3, No. 1, Jan. 1, 2011, pp. 67-75.

Lomino et al., Site-specific chemoenzymatic glycoenginnering of cetuximab, a therapeutic monoclonal antibody (607.16), FASEB Journal, Apr. 1, 2014, 3 pages.

Motiwala et al., "Developing an Alternate Host for Production of Biosimilar Anti-EGFR Monoclonal Antibody," International Journal of Pharmacy and Biological Sciences, vol. 2, No. 4, Jan. 1, 2012, pp. 90-100.

Search Report issued on European Application 15841946.5, dated May 7, 2018.

Van Bueren et al., "Anti-glactose-alpha-1,3-galactose IgE from allergic patients does not bind alpha-galactosylated glycans on intact therapeutic antibody Fc domains," Natural Biotechnology, vol. 29, No. 7, Jul. 1, 2011, pp. 574-576.

Notice of Preliminary Rejection issued for KR 10-2016-7027348, dated Aug. 21, 2018.

Examination Report dated Jun. 5, 2019 in EP Application No. 15841946.5 (8 pages).

International Search Report and Written Opinion on PCT/US2015/050131, dated Jan. 27, 2016.

Mariotte et al., "Anti-cetuximab IgE ELISA for identification of patients at a high risk of cetuximab-induced anaphylaxis," MAbs, Jul. 1, 2011, vol. 3, Iss. 4, pp. 396-401.

Examination Report issued on Australian Application 2015318018, dated Oct. 7, 2016.

\* cited by examiner

FIG. 1
A) Inhibition of phosphorylated EGFR in A549
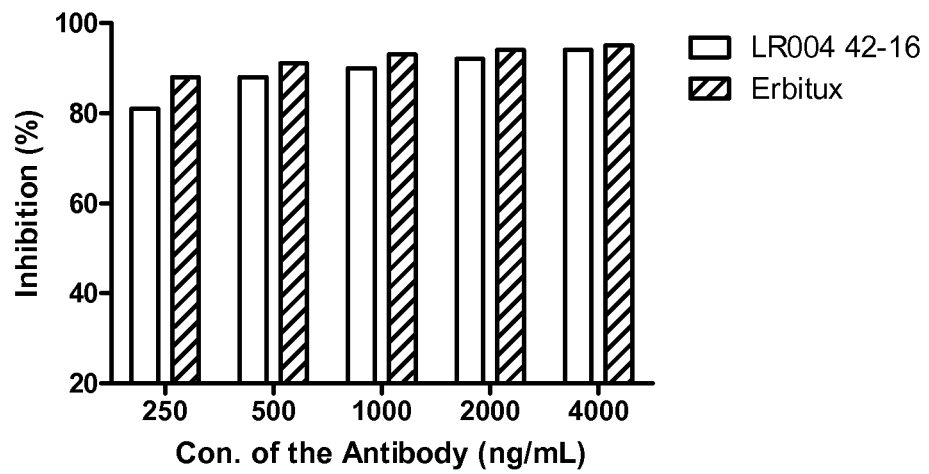
B) Inhibition of phosphorylated EGFR in FaDu
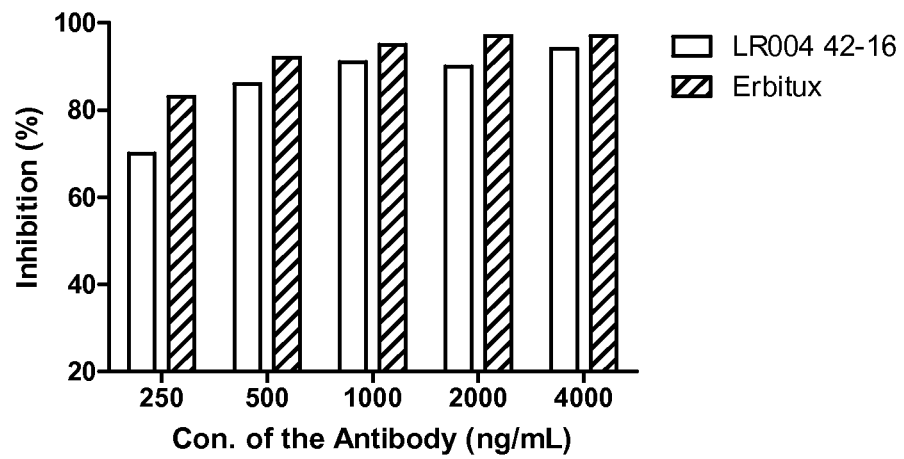

FIG. 3
A) EGFR
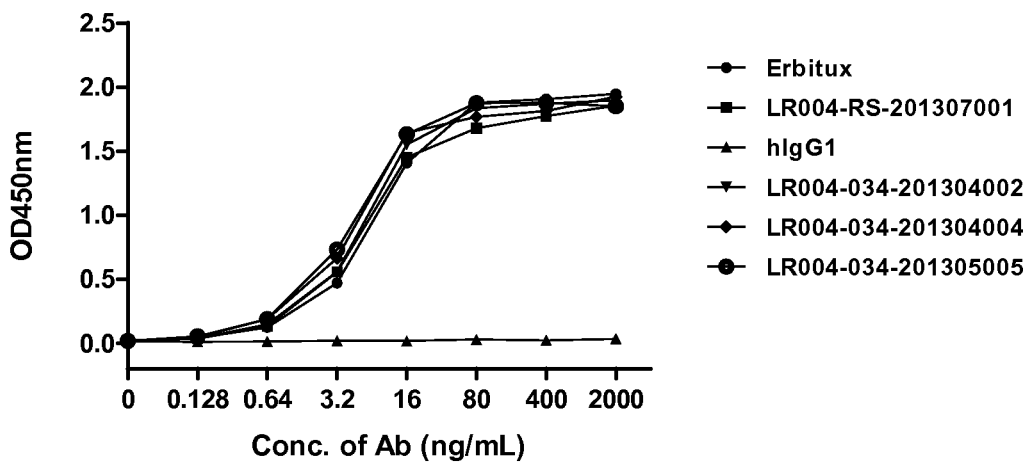
B) HER2
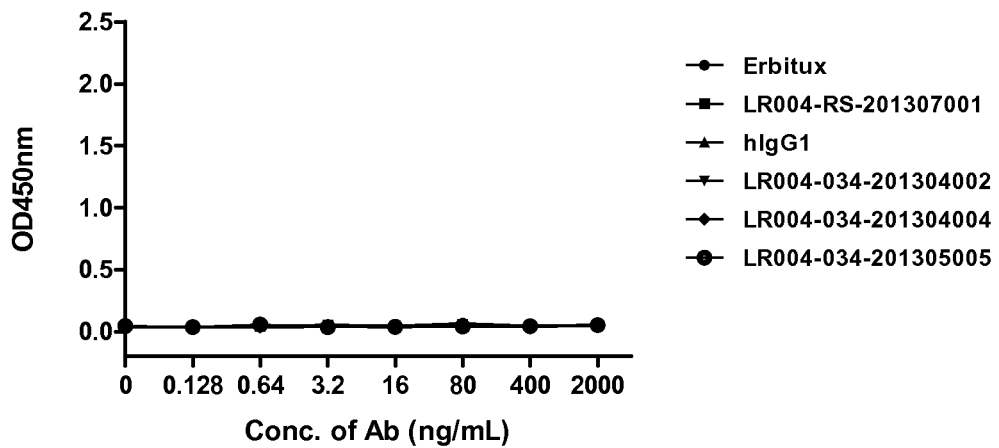

FIG. 6
A) MDA-MB-468
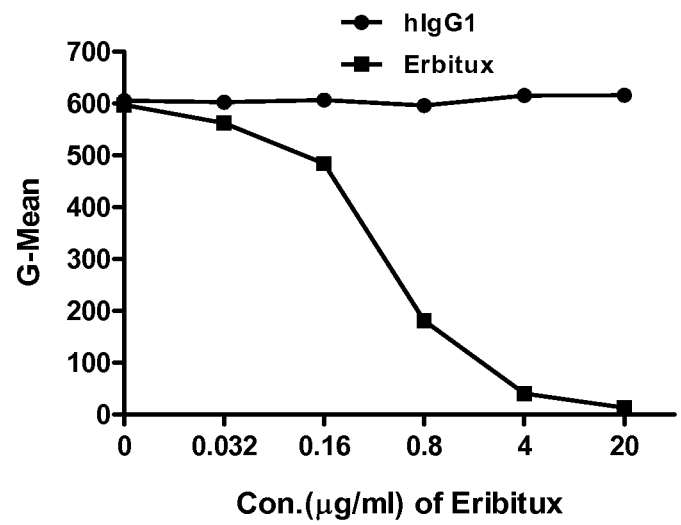
B) FaDU
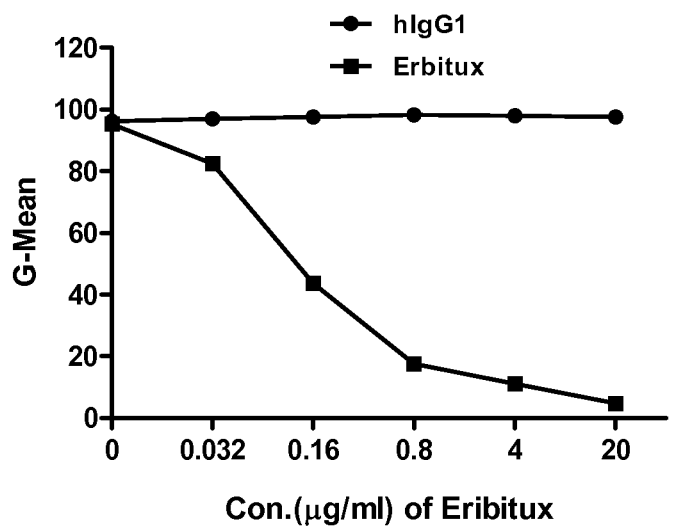

FIG. 8
A) MDA-MB-468
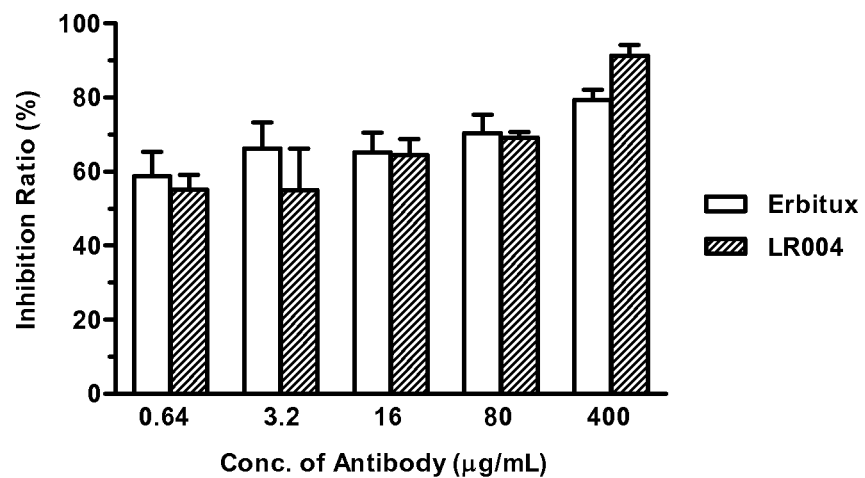
B) LoVo
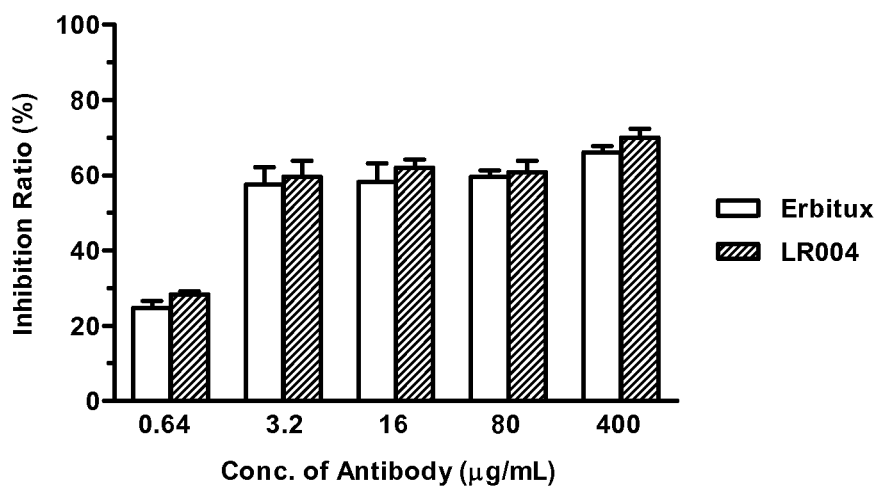

FIG. 8 (cont.)
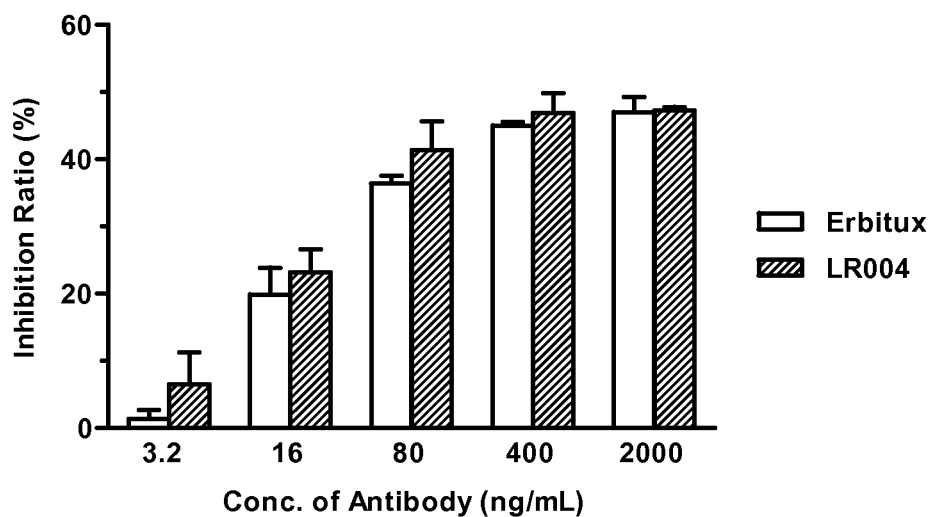
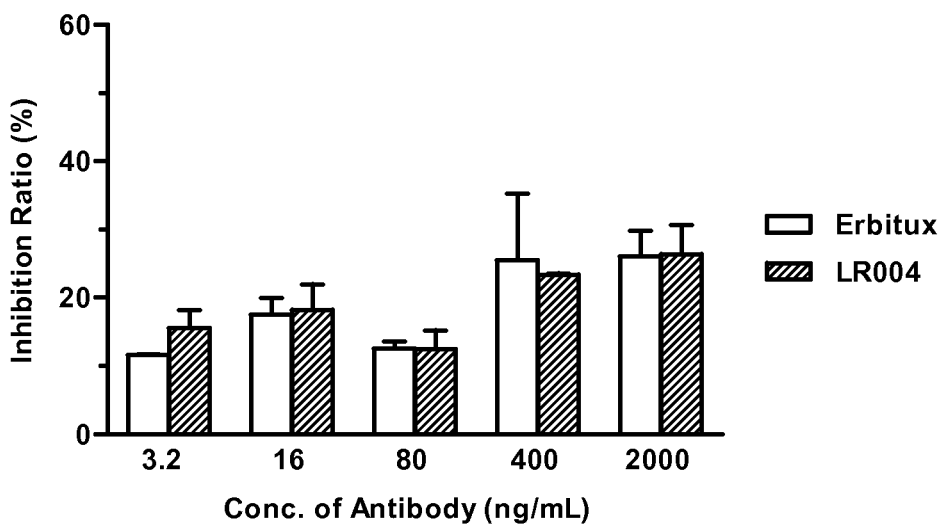

SEQUENCE LISTING

```
<160> NUMBER OF SEQ ID NOS: 4

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Leu Leu Thr Gln Ser Pro Val Ile Leu Ser Val Ser Pro Gly
1               5                   10                  15
```

```
Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

-continued

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Arg Val Glu Pro Lys Ser Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: May or may not be present

<400> SEQUENCE: 3

Gln Val Gln Leu Lys Gln Ser Gly Pro Gly Leu Val Gln Pro Ser
1               5                   10                  15

<210> SEQ ID NO 4
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Ile Leu Leu Thr Gln Ser Pro Val Ile Leu Ser Val Ser Pro
1               5                   10                  15
```

ANTI-EGFR ANTIBODY AND USES OF SAME

CROSS-REFERENCE TO RELATED APPLICATIONS

This application is a 371 National Phase Application of PCT/US2015/050131, filed Sep. 15, 2015, which claims priority to U.S. Provisional Application No. 62/051,126, filed Sep. 16, 2014, which is incorporated herein by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,192 byte ASCII (Text) file named "108973-0117_SL.txt SEQUENCE LISTING" created on Nov. 5, 2010.

FIELD OF THE INVENTION

This disclosure relates generally to the therapeutic uses of an anti-EGFR antibody. In particular, the present disclosure relates to methods and compositions comprising an anti-EGFR antibody for the treatment of EGFR-expressing cancers.

BACKGROUND

The epidermal growth factor receptor (EGFR) is composed of an extracellular ligand-binding domain, a transmembrane segment and an intracellular tyrosine kinase domain. Upon the binding of a ligand such as epidermal growth factor (EGF) and transforming growth factor α (TGFα), the EGFR forms homo or heterodimers with the other members of the ErbB family resulting in autophosphorylation of the intracellular domain and activation of the downstream signaling pathways, including Ras-induced MAP kinase pathway, the PI3-kinase pathway and the JAK/STAT pathway. This can signal cancer cell proliferation, inhibition of apoptosis, and activation of invasion and stimulate tumor-induced neovascularization. Human cancers expressing EGFR are often treated with an EGFR-specific antibody that inhibits receptor signaling and tumor cell proliferation, such as the approved anti-EGFR mAb, cetuximab (Erbitux®).

The direct mechanism of action of cetuximab is the blockade of ligand-receptor binding and thereby inhibition of ligand-mediated activation of the EGFR tyrosine kinase. As a result of this EGFR blockade, a variety of processes regulated by the EGFR-signaling pathways in tumor cells or stromal cells in the tumor microenvironment are disrupted (Fan Z, et al. 1994; Abanell J, et al. 2001; Prewett M, et al. 1996; Huang S M, et al. 1999; Fan Z, et al. 1993a; Fan Z, et al. 1993b). Other mechanisms including antibody-dependent cellular cytotoxicity (ADCC) and receptor internalization are likely to play an important role as well (Kawaguchi Y, et al. 1996; Kimura H, et al. 2007). ADCC is dependent on interactions between the cellular FcγR and the monoclonal antibody, which triggers innate immunologic responses involving natural killer cells, monocytes, macrophages, activated T-lymphocytes and granulocytes. Receptor internalization down regulates the number of available cell surface receptors and could therefore affect EGFR activation.

Hypersensitivity reactions are a frequent side effect of cetuximab, and can prove fatal for recipients. The present disclosure provides alternative EGFR-targeted therapies useful for individuals having sensitivities to cetuximab that preclude its further use. In particular, the disclosure provides an anti-EGFR antibody having the same specificity and efficacy as cetuximab, but having modifications that render it less immunoreactive and more stable than cetuximab. The antibody is useful alone or in combination with one or more additional therapeutic agents for the treatment of EGFR-expressing cancers.

SUMMARY

In one aspect, the present disclosure provides an antibody comprising the amino acid sequences set forth in Table 2. In some embodiments, the antibody comprises N-acetylneuraminic acid (NANA) and lacks galactose-α-1,3-galactose.

In some embodiments, the antibody is conjugated to a detectable marker. In some embodiments, the detectable marker comprises a radionuclide. In some embodiments, the detectable marker comprises a fluorescent label.

In some embodiments, the antibody is conjugated to one or more additional therapeutic agents. In some embodiments, the one or more additional therapeutic agents comprises a chemotherapeutic agent.

In some embodiments, the chemotherapeutic agent is selected from the group consisting of a vinca alkaloid, a microtubule disrupting agent, an anti-angiogenic agent, a therapeutic antibody, an EGFR targeting agent, a tyrosine kinase targeting agent, a transitional metal complex, a proteasome inhibitor, an antimetabolite an alkylating agent, a platinum-based agent, an anthracycline antibiotic, a topoisomerase inhibitor, a macrolide, a retinoid, geldanamycin or a derivative thereof, adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof, topetecan, vinblastine, vincristine, tamoxifen, piposulfan, nab-5404, nab-5800, nab-5801, Irinotecan, HKP, Ortataxel, gemcitabine, Oxaliplatin, Herceptin®, vinorelbine, Doxil®, capecitabine, Alimta®, Avastin®, Velcade®, Tarceva®, Neulasta®, lapatinib, sorafenib, and erlotinib.

In one aspect, the present disclosure provides a composition comprising an antibody comprising the amino acid sequences set forth in Table 2 and a pharmaceutically acceptable carrier or excipient.

In some embodiments, the composition further comprises a chemotherapeutic agent selected from the group consisting of a vinca alkaloid, a microtubule disrupting agent, an anti-angiogenic agent, a therapeutic antibody, an EGFR targeting agent, a tyrosine kinase targeting agent, a transitional metal complex, a proteasome inhibitor, an antimetabolite an alkylating agent, a platinum-based agent, an anthracycline antibiotic, a topoisomerase inhibitor, a macrolide, a retinoid, geldanamycin or a derivative thereof, adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof, topetecan, vinblastine, vincristine, tamoxifen, piposulfan, nab-5404, nab-5800, nab-5801, Irinotecan, HKP, Ortataxel, gemcitabine, Oxaliplatin, Herceptin®, vinorelbine, Doxil®, capecitabine, Alimta®, Avastin®, Velcade®, Tarceva®, Neulasta®, lapatinib, sorafenib, and erlotinib.

In one aspect, the present disclosure provides a Chinese hamster ovary (CHO) cell comprising nucleic acids encoding an antibody comprising the amino acid sequences set forth in Table 2. In some embodiments, the nucleic acids are present on a replicable vector separate from the CHO cell genome. In some embodiments, the nucleic acids are stably integrated into the CHO cell genome.

In one aspect, the present disclosure provides a method for treating cancer in a subject in need thereof, comprising administering to the subject an antibody comprising the amino acid sequences set forth in Table 2.

In some embodiments, the method further comprises administering one or more additional therapeutic agents selected from the group consisting of a vinca alkaloid, a microtubule disrupting agent, an anti-angiogenic agent, a therapeutic antibody, an EGFR targeting agent, a tyrosine kinase targeting agent, a transitional metal complex, a proteasome inhibitor, an antimetabolite an alkylating agent, a platinum-based agent, an anthracycline antibiotic, a topoisomerase inhibitor, a macrolide, a retinoid, geldanamycin or a derivative thereof, adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof, topetecan, vinblastine, vincristine, tamoxifen, piposulfan, nab-5404, nab-5800, nab-5801, Irinotecan, HKP, Ortataxel, gemcitabine, Oxaliplatin, Herceptin®, vinorelbine, Doxil®, capecitabine, Alimta®, Avastin®, Velcade®, Tarceva®, Neulasta®, lapatinib, sorafenib, and erlotinib.

In some embodiments, the antibody is conjugated to one or more additional therapeutic agents. In some embodiments, the one or more additional therapeutic agents comprises a chemotherapeutic agent. In some embodiments, the chemotherapeutic agent is selected from the group consisting of a vinca alkaloid, a microtubule disrupting agent, an anti-angiogenic agent, a therapeutic antibody, an EGFR targeting agent, a tyrosine kinase targeting agent, a transitional metal complex, a proteasome inhibitor, an antimetabolite an alkylating agent, a platinum-based agent, an anthracycline antibiotic, a topoisomerase inhibitor, a macrolide, a retinoid, geldanamycin or a derivative thereof, adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof, topetecan, vinblastine, vincristine, tamoxifen, piposulfan, nab-5404, nab-5800, nab-5801, Irinotecan, HKP, Ortataxel, gemcitabine, Oxaliplatin, Herceptin®, vinorelbine, Doxil®, capecitabine, Alimta®, Avastin®, Velcade®, Tarceva®, Neulasta®, lapatinib, sorafenib, and erlotinib.

In some embodiments, the subject has elevated levels of anti-cetuximab IgE compared to a negative control sample. In some embodiments, the subject has elevated levels of anti-galactose-α-1,3-galactose IgE compared to a negative control sample.

In some embodiments, the method further comprises determining whether the subject is hypersensitive to cetuximab or is predisposed to having a hypersensitivity reaction to cetuximab. In some embodiments, determining comprises measuring the presence of anti-cetuximab or anti-galactose-α-1,3-galactose IgE in a sample of serum from the subject, wherein an elevated level of anti-cetuximab or anti-galactose-α-1,3-galactose IgE compared to a negative control sample indicates that the subject is hypersensitive to cetuximab or is predisposed to having a hypersensitivity reaction to cetuximab. In some embodiments, measuring comprises the use of an enzyme-linked immunosorbent assay (ELISA).

In one aspect, the present disclosure provides a method of producing an antibody comprising the amino acid sequences set forth in Table 2, comprising contacting a Chinese hamster ovary (CHO) cell with nucleic acids encoding the amino acid sequence set forth in Table 2. In some embodiments, the nucleic acids are stably integrated into the genome of the CHO cell.

BRIEF DESCRIPTION OF THE DRAWINGS

The figures included herein depict non-limiting exemplary embodiments of the technology disclosed herein and are provided to aid the reader in understanding the disclosure.

FIG. 1A-B are charts showing inhibition of TGF-induced phosphorylation of EGFR by LR004 and Erbitux® in the tumor cell lines A549 and FaDu.

FIG. 8A-D are charts showing the effect of LR004 or Erbitux® on the in vitro growth of tumor cell lines. Cell lines tested included A) MDA-MB-468 breast carcinoma cells, B) Colon Cancer Cell line LoVo, C) Hypopharyngeal carcinoma Line FaDu and D) A431 Epidermoid Carcinoma cells. In vitro growth inhibition by LR004 and Erbitux® was determined by either CCK-8 (A and B) or ATPLite (C and D) assays.

DETAILED DESCRIPTION OF THE INVENTION

I. General

Figure 2:
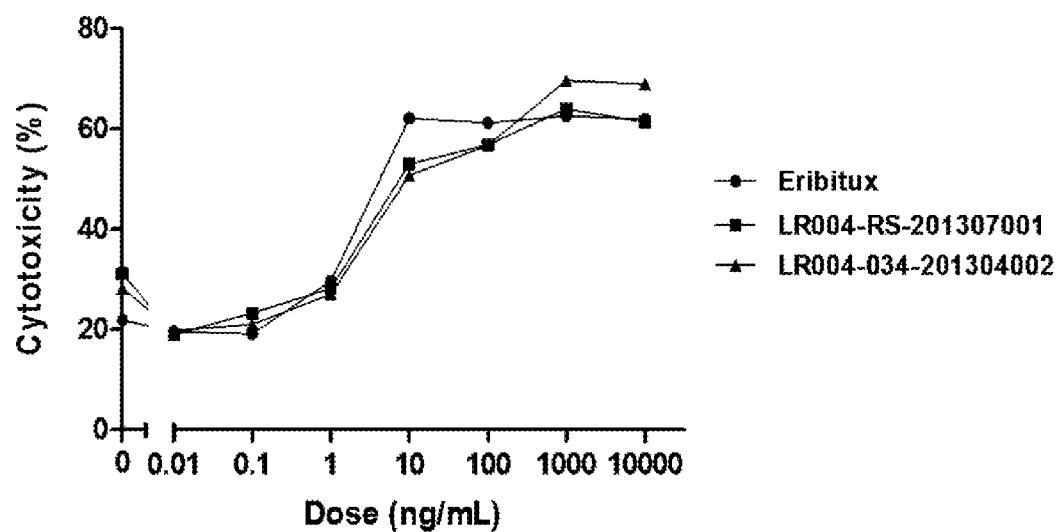
FIG. 2 is a chart showing ADCC the effect of LR004 and Erbitux® on hypopharyngeal carcinoma FaDu cells.

The present disclosure provides methods and compositions comprising an EGFR-specific antibody useful for treating EGFR-expressing cancers. It is to be appreciated that certain aspects, modes, embodiments, variations and features of the technology disclosed herein are described below in various levels of detail in order to provide a substantial understanding technology.

Unless defined otherwise, all technical and scientific terms used herein generally have the same meaning as commonly understood by one of ordinary skill in the art to which this technology belongs. As used in this specification and the appended claims, the singular forms "a," "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art. Standard techniques are used for nucleic acid and peptide synthesis. Standard techniques, or modifications thereof, are used for chemical syntheses and chemical analyses. All references cited herein are incorporated herein by reference in their entireties and for all purposes to the same extent as if each individual publication, patent, or patent application was specifically and individually incorporated by reference in its entirety for all purposes.

The definitions of certain terms as used in this specification are provided below. Definitions of other terms may be found in the *Illustrated Dictionary of Immunology*, 2nd Edition (Cruse, J. M. and Lewis, R. E., Eds., Boca Raton, Fla.: CRC Press, 1995).

As used herein, the term "synergy" or "synergist" refers to an effect arising between two or more agents, entities, factors, or substances that produces an effect greater than the sum of their individual effects. In some embodiment, synergy between biologically active agents, such as the LR004 antibody and a chemotherapeutic agent is determined via the coefficient of drug interaction (i.e., CDI) (see e.g., Cao S S, et al., Potentiation of antimetabolite antitumor activity in vivo by dipyridamole and amphotericin B. *Cancer Chemother Pharmacol* 1989; 24: 181-186). In some embodiments, CDI is calculated as follows: CDI=AB/A×B. According to the chemiluminescence of each group, AB is the ratio of the combination groups to the control group; A or B is the ratio of the single agent group to the control group. The drug combination is synergistic when the CDI value is less than 1. In determining a synergistic interaction between two or more components, in some embodiments, the optimum range for the effect, and the absolute dose range of each component for the effect, may be measured by administration of the components over different w/w ratio ranges and/or different doses to patients in need of treatment. The observation of synergy in one species can be predictive of the effect in other species, and the results of such studies can be used to predict effective dose.

As used herein, the term "significant synergy" or "significantly synergistic" refers to an effect arising between two or more agents, entities, factors, or substances that produces an effect statistically significantly greater than the sum of their individual effects. By way of example, but not by way of limitation, a drug combination is significantly synergistic when the CDI value is less than 0.7.

As used herein, the term "additive" refers to an effect arising between two or more agents, entities, factors, or substances that produces an effect equal to the sum of their individual effects.

As used herein, the term "antergy" or "antagonistic" refers to an effect arising between two or more agents, entities, factors, or substances that produces an effect less than the sum of their individual effects. By way of example, but not by way of limitation, a drug combination is additive when the CDI value is greater than 1.

As used herein, the term "EGFR" refers to cell surface receptor for members of the epidermal growth factor (EGF) family of extracellular protein ligands. The receptor is a member of four related receptor tyrosine kinases (RTK): EGFR (ErbB-1), HER2/c-neu (ErbB-2), Her 3 (ErbB-3), and Her 4 (ErbB-4). As well-known in the art, mutational activation of EGFR can lead to ligand-independent signaling, promotion of cell proliferation and growth, and the development of various cancers.

As used herein, the administration of an agent or drug to a subject includes self-administration and the administration by another. It is also to be appreciated that the various modes of treatment or prevention of medical conditions as described are intended to mean "substantial," which includes total but also less than total treatment or prevention, and wherein some biologically or medically relevant result is achieved.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

As used herein, the term "antibody" means a polypeptide comprising a framework region from an immunoglobulin gene or fragments thereof that specifically binds and recognizes an antigen, e.g., EGFR. Use of the term antibody is meant to include whole antibodies, including single-chain whole antibodies, and antigen-binding fragments thereof. The term "antibody" includes bispecific antibodies and multispecific antibodies so long as they exhibit the desired biological activity or function.

As used herein, the term "antibody-related polypeptide" means antigen-binding antibody fragments, including single-chain antibodies, that can comprise the variable region(s) alone, or in combination, with all or part of the following polypeptide elements: hinge region, $CH_1$, $CH_2$, and $CH_3$ domains of an antibody molecule. Also included in the disclosure are any combinations of variable region(s) and hinge region, $CH_1$, $CH_2$, and $CH_3$ domains. Antibody-molecules of the present technology include, e.g., but are not limited to, Fab, Fab' and $F(ab')_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a $F(ab')_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward, et al., *Nature* 341: 544-546, 1989), which consists of a $V_H$ domain; and (vi) an isolated complementarity determining region (CDR). As such "antibody fragments" can comprise a portion of a full length antibody, generally the antigen binding or variable region thereof. Examples of antibody fragments include Fab, Fab', $F(ab')_2$, and Fv fragments; diabodies; linear antibodies; single-chain antibody molecules; and multispecific antibodies formed from antibody fragments. Single-chain antibody molecules may comprise a polymer with a number of individual molecules, for example, dimmer, trimer or other polymers.

As used herein, the term "biological sample" means sample material derived from or contacted by living cells. The term "biological sample" is intended to include tissues, cells and biological fluids isolated from a subject, as well as tissues, cells and fluids present within a subject. Biological samples of the present technology include, e.g., but are not limited to, whole blood, plasma, semen, saliva, tears, urine, fecal material, sweat, buccal, skin, cerebrospinal fluid, and hair. Biological samples can also be obtained from biopsies of internal organs or from cancers.

As used herein, the term "CDR-grafted antibody" means an antibody in which at least one CDR of an "acceptor" antibody is replaced by a CDR "graft" from a "donor" antibody possessing a desirable antigen specificity.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson, et al., PCT/US86/02269; Akira, et al., European Patent Application 184,187; Taniguchi, European Patent Application 171, 496; Morrison, et al., European Patent Application 173,494; Neuberger, et al., WO 86/01533; Cabilly, et al. U.S. Pat. No. 4,816,567; Cabilly, et al., European Patent Application 125, 023; Better, et al., Science 240: 1041-1043, 1988; Liu, et al., *Proc Natl Acad Sci USA* 84: 3439-3443, 1987; Liu, et al., *J Immunol* 139: 3521-3526, 1987; Sun, et al., *Proc Natl Acad Sci USA* 84: 214-218, 1987; Nishimura, et al., *Cancer Res* 47: 999-1005, 1987; Wood, et al., *Nature* 314: 446-449, 1885; and Shaw, et al., *J Natl Cancer Inst* 80: 1553-1559, 1988.

As used herein, the term "comparison window" means a segment of any one of the number of contiguous positions selected from the group consisting of from 20 to 600 amino acids or nucleotides, usually about 50 to about 200, more usually about 100 to about 150 in which a sequence can be compared to a reference sequence of the same number of contiguous positions after the two sequences are optimally aligned.

As used herein, the term "consensus FR" means a framework (FR) antibody region in a consensus immunoglobulin sequence. The FR regions of an antibody do not contact the antigen.

As used herein, the term "consensus sequence" refers to the sequence formed from the most frequently occurring amino acids (or nucleotides) in a family of related sequences (See e.g., Winnaker, *From Genes to Clones* (Verlagsgesellschaft, Weinheim, Germany 1987). That is, in a family of proteins, each position in the consensus sequence is occupied by the amino acid occurring most frequently at that position in the family. If two amino acids occur equally frequently, either can be included in the consensus sequence.

As used herein, the term "contacted" when applied to a cell or tissue refers to the process by which an EGFR antibody of the present technology, antibody composition, cytotoxic agent or moiety, gene, protein and/or antisense sequence, is delivered to a target cell or is placed in direct proximity with the target cell. This delivery can be in vitro or in vivo and can involve the use of a recombinant vector system.

As used herein, the term "cytotoxic moiety" means a moiety that inhibits cell growth or promotes cell death when proximate to or absorbed by a cell. Suitable cytotoxic moieties in this regard include radioactive agents or isotopes (radionuclides), chemotoxic agents such as differentiation inducers, inhibitors and small chemotoxic drugs, toxin proteins and derivatives thereof, as well as nucleotide sequences (or their antisense sequence). Therefore, the cytotoxic moiety can be, by way of non-limiting example, a chemotherapeutic agent, a photoactivated toxin or a radioactive agent.

As used herein, the term "diabodies" refers to small antibody fragments with two antigen-binding sites, which fragments comprise a heavy-chain variable domain ($V_H$) connected to a light-chain variable domain ($V_L$) in the same polypeptide chain ($V_H V_L$). By using a linker that is too short to allow pairing between the two domains on the same chain, the domains are forced to pair with the complementary domains of another chain and create two antigen binding sites. Diabodies are described more fully in, e.g., EP 404, 097; WO 93/11161; and 30 Hollinger, et al., Proc. Natl. Acad. Sci. USA, 90: 6444-6448 (1993).

As used herein, the term "effective amount" of a composition, is a quantity sufficient to achieve a desired therapeutic and/or prophylactic effect, e.g., an amount which results in the prevention of, or a decrease in, the symptoms associated with a disease that is being treated, e.g., the diseases associated with target polypeptide. The amount of a composition of the present technology administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present technology can also be administered in combination with each other, or with one or more additional therapeutic compounds.

As used herein, "expression" includes but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, the term "gene" means a segment of DNA that contains all the information for the regulated biosynthesis of an RNA product, including promoters, exons, introns, and other untranslated regions that control expression.

As used herein, the term "genotype" means an unphased 5' to 3' sequence of nucleotide pairs found at one or more polymorphic or mutant sites in a locus on a pair of homologous chromosomes in an individual. As used herein, genotype includes a full-genotype and/or a sub-genotype.

As used herein, the term "human sequence antibody" includes antibodies having variable and constant regions (if present) derived from human germline immunoglobulin sequences. The human sequence antibodies of the present technology can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT Publication Nos. WO 01/14424 and WO 00/37504. However, the term "human sequence antibody," as used herein, is not intended to include antibodies in which CDR sequences derived from the germline of another mammalian species, such as a mouse, have been grafted onto human framework sequences (e.g., humanized antibodies).

As used herein, the term "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optionally also will comprise at least a portion of an immunoglobulin constant region (Fc), typically that of a human immunoglobulin. For further details, see Jones, et al., Nature 321: 522-525 (1986); Reichmann, et al., Nature 332:323-329 (1988); and Presta, Curr. Op. Struct. Biol. 2:593-596 (1992).

In one embodiment, the present disclosure contemplates amino acid modifications of the EGFR antibody of the present technology. For example, it may be desirable to improve the binding affinity and/or other biological properties of the antibody Amino acid sequence variants of the EGFR antibody may be prepared by introducing appropriate nucleotide changes into the antibody nucleic acid, or by peptide synthesis. Such modifications include, for example, deletions from, and/or insertions into and/or substitutions of, residues within the amino acid sequences of the EGFR binding site. Any combination of deletion, insertion, and substitution is made to obtain the antibody of interest, as long as the obtained antibody possesses the desired properties, e.g., biological activity. The modification also includes the change of the pattern of glycosylation of the protein. A useful method for identification of preferred locations for mutagenesis is called "alanine scanning mutagenesis" as described by Cunningham and Wells in Science, 244:1081-1085 (1989). The mutated antibody is then screened for the desired activity.

As used herein, the term "hypervariable region" refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 31-35B (H1), 50-65 (H2) and 95-102 (H3) in the $V_H$ (Kabat, et al., Sequences of Proteins of Immunological Interest, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk J. Mol. Biol. 196:901-917 (1987)).

As used herein, the terms "identical" or percent "identity," when used in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This term also refers to, or can be applied to, the compliment of a test sequence. The term also includes sequences that have deletions and/or additions, as well as those that have substitutions. As described below, the preferred algorithms can account for gaps and the like. In some embodiments, identity exists over a region that is at least about 25 amino acids or nucleotides in length; additionally or alternatively, in some embodiments, identity exists over a region that is 50-100 amino acids or nucleotides in length.

An "isolated" or "purified" polypeptide or biologically-active portion thereof is substantially free of cellular material or other contaminating polypeptides from the cell or tissue source from which the polypeptide is derived, or substantially free from chemical precursors or other chemicals when chemically synthesized. For example, an isolated EGFR antibody is one substantially free of cellular material or other contaminating polypeptides from the cell or tissue source from which the antibody is derived. Such contaminating polypeptides may include enzymes, hormones and other proteinaceous and nonproteinaceous solutes, which may or may not interfere with the biological activity of the antibody.

As used herein, the phrase "induce cell death" or "capable of inducing cell death" refers to ability of an agent to cause a viable cell become nonviable. In some embodiments, the LR004 antibody induces cell death in cancer cell in vitro or in vivo. Cell death and cell viability can be determined by various method in the art such as trypan blue exclusion assay and other cell viability assays. In the present technology, the cell death refers to "apoptosis," also known as "programmed cell death," which is indicated by caspase activation, the binding of Annexin V to the cell surface, DNA fragmentation, the loss of cellular volume, dilation of endoplasmic reticulum, cell fragmentation, and/or formation of membrane vesicles (apoptotic bodies). Apoptosis can be measured using methods known in the art, including but not limited to detection of Annexin V staining, DNA fragmentation, or caspase activation.

As used herein, the term "intact antibody" means an antibody that has at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present technology may be made by the hybridoma method first described by Kohler, et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson, et al., Nature 352:624-628 (1991) and Marks, et al., J. Mol. Biol. 222:581-597 (1991), for example.

As used herein, the term "medical condition" includes, but is not limited to, any condition or disease manifested as one or more physical and/or psychological symptoms for which treatment and/or prevention is desirable, and includes previously and newly identified diseases and other disorders.

As used herein, the term "modulator" includes inhibitors and activators. Inhibitors are agents that, e.g., bind to, partially or totally block stimulation, decrease, prevent, delay activation, inactivate, desensitize, or down regulate the activity of a target molecule. Activators are agents that, e.g., bind to, stimulate, increase, open, activate, facilitate, enhance activation, sensitize or up regulate the activity of a target molecule. In some embodiments, the target molecule is an EGFR receptor. Modulators include genetically modified versions of a naturally-occurring ligand for the target molecule, as well as naturally-occurring and synthetic ligands, antagonists, agonists, small chemical molecules and the like.

As used herein, the term "neutralizing antibody" means an antibody molecule that is able to eliminate or significantly reduce at least one (1) biological function of a target molecule. In some embodiments, the target molecule is an EGFR receptor.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration.

As used herein, the terms "polypeptide," "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature. In a particular embodiment, the polypeptide contains polypeptide sequences from an EGFR receptor.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, e.g., recombinant cells express genes that are not found within the native (non-recombinant) form of the cell or express native genes that are otherwise abnormally expressed, under expressed or not expressed at all.

As used herein, the phrase "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule To increase the serum half-life of the antibody, one may incorporate a salvage receptor binding epitope into the antibody (especially an antibody fragment) as described in U.S. Pat. No. 5,739,277, for example.

As used herein, the terms "single chain antibodies" or "single chain Fv (scFv)" refer to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv). See, e.g., Bird, et al., Science 242: 423-426, 1988; and Huston, et al., Proc. Natl. Acad. Sci.

USA, 85: 5879-5883, 1988). Such single chain antibodies are included by reference to the term "antibody" fragments, and can be prepared by recombinant techniques or enzymatic or chemical cleavage of intact antibodies.

As used herein, the term "small molecule" means a composition that has a molecular weight of less than about 5 kDa and more preferably less than about 2 kDa. Small molecules can be, e.g., nucleic acids, peptides, polypeptides, glycopeptides, peptidomimetics, carbohydrates, lipids, lipopolysaccharides, combinations of these, or other organic or inorganic molecules.

As used herein, the term "specific binding" of a receptor and ligand means the contact between a receptor and ligand having a binding affinity of at least $10^{-6}$ M. In some embodiments, ligands bind with affinities of at least about $10^{-7}$ M, $10^{-8}$ M, $10^{-9}$ M, $10^{-10}$ M, $10^{-11}$ M, or $10^{-12}$ M. In some embodiments, the receptor and ligand are EGFR and an EGFR antibody. In some embodiments, the EGFR antibody is the LR004 antibody.

As used herein, the phrase "stringent hybridization conditions" means conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can also be achieved with the addition of destabilizing agents such as formamide. For selective or specific hybridization, a positive signal is at least two times background, preferably 10 times background hybridization. Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C.

As used herein, the term "subject" refers to an animal, preferably a mammal, such as a human, but can also be another mammal, e.g., domestic animals (e.g., dogs, cats and the like), farm animals (e.g., cows, sheep, pigs, horses and the like) and laboratory animals (e.g., monkey, rats, mice, rabbits, guinea pigs and the like).

As used herein, the term "amino acid substitution" refer to the alteration of an amino acid within a peptide to a different amino acid. As known in the art, amino acid substitutions may be "conservative" or "non-conservative" depending on their effects on the biological activity of the peptide. So-called "conservative substitutions" are shown in the Table below under the heading of "preferred substitutions".

TABLE 1

Amino Acid Substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

As used herein, the term "target cell" means any cell in a subject (e.g., a human or animal) that can be targeted by the EGFR antibody of the present technology.

As used herein, the term "therapeutic agent" is intended to mean a compound that, when present in an effective amount, produces a desired therapeutic effect on a subject in need thereof.

As used herein, the terms "treating" or "treatment" or "alleviation" refers to therapeutic treatment. A subject is successfully "treated" for a cancer in which cancer cells expressing EGFR where, after receiving a therapeutic amount of EGFR antibody, the subject shows observable and/or measurable reduction in or absence of one or more signs and symptoms of cancer, such as, including but not limited to, a reduction in the number of cancer cells present in the individual; a reduction in tumor size, weight, volume, or number, inhibition of tumor growth and/or metastasis, an increase in the length of remission, reduction or relief of pain, a reduction in morbidity and mortality; an increase in body weight, or a general improvement in the quality of life. "Prevention" or "preventing" a disease or condition refers to prophylactic or preventative measures, wherein the object is to prevent or slow down (lessen) the targeted pathologic condition or disorder.

As used herein, the term "variable" refers to the fact that certain segments of the variable domains differ extensively in sequence among antibodies. The V domain mediates antigen binding and define specificity of a particular antibody for its particular antigen. However, the variability is not evenly distributed across the amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat, et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody ADCC.

II. LR004 Antibody and Antibody Conjugates

LR004 is a recombinant, human/mouse chimeric monoclonal antibody that binds specifically to the N-terminal portion of a human epidermal growth factor receptor (EGFR). EGFR is a member of the human epidermal growth factor receptor (HER) or ErbB family, also known as the type 1 receptor tyrosine kinase or ErbB1/HER1. The other members of the family include ErbB2 (HER2/neu), ErbB3 (HER3) and ErbB4 (HER4). EGFR signaling in tumor cells is responsible for regulating a diverse network of cellular functions that influence neoplastic growth including proliferation, survival, damage repair, adhesion, migration, and neovascularization. EGFR is expressed at various levels in a number of human cancers of epithelial origin. Epithelial tumors that commonly express EGFR include bladder, breast, cervix, colon, head and neck, kidney, lung, pancreatic, and prostate. Misregulation of EGFR, through overexpression or mutation, leads to constitutive activity or impaired receptor down-regulation and can cause malignant transformation of the cell. The oncogenic effects of EGFR include initiation of DNA synthesis, enhanced cell growth, invasion, and metastasis.

LR004 is an improved version of cetuximab, having the same mechanisms of action, including blockade of EGFR ligand binding leading to inhibition of downstream effects, such as inhibition of intracellular signaling, inhibition of cell cycle progression, induction of apoptosis, and inhibition of DNA repair, angiogenesis, tumor cell motility, invasion, and metastasis. Studies demonstrating LR004 inhibition of TGF-induced phosphorylation of EGFR, stimulation of ADCC, and anti-tumorigenic effects in vitro and in vivo are presented below. LR004 is less likely to induce hypersensitivity reactions than cetuximab due to differences in post-translational carbohydrate modification, and is useful for the treatment of subjects who are unable to continue cetuximab treatment because of these side effects.

The amino acid sequence of LR004 was modified from the cetuximab sequence published in the Drug Bank (Accession Number: DB00002). A comparison of the sequences of LR004 and the commercially available cetuximab was performed by LC-MS/MS analyses. Although the Fab sequence of LR004 is identical to that of cetuximab, the Fc sequence differs by 5 amino acids, shown in bold in Table 2. LR004 has a Pro-Lys-Ser repeat at residues 222 to 224 of the heavy chain, whereas cetuximab does not contain the repeat. The residues of CH3 Aspartate361 and Leucine363 are present in LR004. In contrast, CH3 Glutamate361 and Methionine363 are found in cetuximab. These differences represent different IgG1 Fc allotypes of LR004 (G1m1, 17) and cetuximab (G1m3). Both allotypes are common among the approved monoclonal antibodies. The amino acid sequences of the light chain and the variable region of the heavy chain are identical to those of the cetuximab.

The theoretical molecular weights of the light and heavy chains of LR004 are 23718 Da (alkylated LC) and 53037 Da (alkylated HC, G0F/G0F), respectively. The functional LR004 consists of four polypeptide chains and an apparent molecular weight of ≈200 KDa by non-reduced SDS-PAGE. Characteristic for LR004 is a multitude of bands detectable by IEF between pI marker bands 7.0 and 8.6, representing different charge isoforms of LR004.

The LR004 antibody comprises two differences in carbohydrate structure compared to cetuximab, owing to aspects of its production. While cetuximab is expressed in SP2/0 cells, LR004 is expressed in Chinese Hamster Ovary (CHO) cells. As a result, the sialic acid of the LR004 is N-acetyl-neuraminic acid (NANA) as opposed to N-glycolyl-neuraminic acid (NGNA) on cetuximab. NANA is considered to be more human-like than NGNA. In addition, while cetuximab contains a high-level of galactose-α-1,3-galactose (Galα1,3Gal), a potent oligosaccharide immunogen, LR004 contains no detectable amount of such carbohydrate structure. Expression in CHO cells gives LR004 a glycan profile that is notably much less immunoreactive than that of cetuximab. With these two modifications, LR004 is a safer product than cetuximab but having the same mechanism of action and efficacy. As shown below, LR004 also demonstrates a longer serum half-life than cetuximab in repeat-dosage treatment regimens, and increased thermostability.

The amino acid sequence of LR004 is given in Table 2. The light chain contains 214 amino acids and the heavy chain contains 452 amino acids. The sequence of the light chain is identical to that of cetuximab. In Table 2, the position of disulfide bonds are shown as connected straight lines and two occupied N-glycan sites on the heavy chain are underlined, one within the framework 3 of the variable (Fv) region at $Asn^{88}$ with a range of sugars, including sialic acid, N-acetylneuraminic acid (NANA) and the other within the CH2 domain at $Asn^{302}$. There is one N-terminal pyroglutamate on the heavy chain. Physiochemical and biological properties of the LR004 antibody are summarized in Table 3.

As described in the Examples included herein, LR004 binds specifically to human EGFR, and inhibits the growth and signaling of EGFR-expressing tumor cells. In vitro studies demonstrate the effects of LR004 on EGFR phosphorylation and on ADCC in hypophyrangeal carcinoma (FaDu) cells. Pharmacodynamic assessments described include ELISA and SPR-based binding affinity studies, ELISA binding specificity study as well as flow-cytometric evaluation of LR004 binding to intact tumor cells in vitro. Anti-tumor activity is also shown in vitro in human cancer cell lines and in vivo in mouse xenograft studies with human colon cancer GEO cell-derived tumors. Additional in vivo efficacy studies will demonstrate further the efficacy of LR004 as compared cetuximab.

LR004 is useful for the treatment of EGFR-expressing cancers, administered either alone, or in combination with one or more additional therapeutic agents. In particular, LR004 is useful for treating patients having hypersensitivity to cetuximab that precludes continued therapy with cetuximab.

TABLE 2

LR004 Amino Acid Sequence

LR004 Light Chain (L-Chain) (SEQ ID NO: 1)

1   Asp-Ile-Leu-Leu-Thr-Gln-Ser-Pro-Val-Ile-Leu-Ser-Val-Ser-Pro-Gly-Glu-Arg-Val-Ser-Phe-Ser-Cys²³-Arg-Ala

26  Ser-Gln-Ser-Ile-Gly-Thr-Asn-Ile-His-Trp-Tyr-Gln-Gln-Arg-Thr-Asn-Gly-Ser-Pro-Arg-Leu-Leu-Ile-Lys-Tyr

51  Ala-Ser-Glu-Ser-Ile-Ser-Gly-Ile-Pro-Ser-Arg-Phe-Ser-Gly-Ser-Gly-Ser-Gly-Thr-Asp-Phe-Thr-Leu-Ser-Ile

76  Asn-Ser-Val-Glu-Ser-Glu-Asp-Ile-Ala-Asp-Tyr-Tyr-Cys⁸⁸-Gln-Gln-Asn-Asn-Asn-Trp-Pro-Thr-Thr-Phe-Gly-Ala

101 Gly-Thr-Lys-Leu-Glu-Leu-Lys-Arg-Thr-Val-Ala-Ala-Pro-Ser-Val-Phe-Ile-Phe-Pro-Pro-Ser-Asp-Glu-Gln-Leu

126 Lys-Ser-Gly-Thr-Ala-Ser-Val-Val-Cys¹³⁴-Leu-Leu-Asn-Asn-Phe-Tyr-Pro-Arg-Glu-Ala-Lys-Val-Gln-Trp-Lys-Val

151 Asp-Asn-Ala-Leu-Glu-Ser-Gly-Asn-Ser-Gln-Glu-Ser-Val-Thr-Glu-Gln-Asp-Ser-Lys-Asp-Ser-Thr-Tyr-Ser-Leu

176 Ser-Ser-Thr-Leu-Thr-Leu-Ser-Lys-Ala-Asp-Tyr-Glu-Lys-His-Lys-Val-Tyr-Ala-Cys¹⁹⁴-Glu-Val-Thr-His-Gln-Gly

201 Leu-Ser-Ser-Pro-Val-Thr-Lys-Ser-Phe-Asn-Arg-Gly-Glu-Cys²¹⁴

LR004 Heavy Chain (H-Chain) (SEQ ID NO: 2)

1   Gln-Val-Gln-Leu-Lys-Gln-Ser-Gly-Pro-Gly-Leu-Val-Gln-Pro-Ser-Gln-Ser-Leu-Ser-Ile-Thr-Cys²²-Thr-Val-Ser

26  Gly-Phe-Ser-Leu-Thr-Asn-Tyr-Gly-Val-His-Trp-Val-Arg-Gln-Ser-Pro-Gly-Lys-Gly-Leu-Glu-Trp-Leu-Gly-Val

51  Ile-Trp-Ser-Gly-Gly-Asn-Thr-Psp-Tyr-Asn-Thr-Pro-Phe-Thr-Ser-Arg-Leu-Ser-Ile-Asn-Lys-Asp-Asn-Ser-Lys

76  Ser-Gln-Val-Phe-Phe-Lys-Met-Asn-Ser-Leu-Gln-Ser-Asn⁸⁸-Asp-Thr-Ala-Ile-Tyr-Tyr-Cy⁹⁵-Ala-Arg-Ala-Leu-Thr

101 Tyr-Tyr-Asp-Tyr-Glu-Phe-Ala-Tyr-Trp-Gly-Gln-Gly-Thr-Leu-Val-Thr-Val-Ser-Ala-Ala-Ser-Thr-Lys-Gly-Pro

126 Ser-Val-Phe-Pro-Leu-Ala-Pro-Ser-Ser-Lys-Ser-Thr-Ser-Gly-Gly-Thr-Ala-Ala-Leu-ray-Cys¹⁴⁶-Leu-Val-Lys-Asp 151 Tyr-Phe-Pro-Glu-Pro-Val-Thr-Val-Ser-Trp-Asn-Ser-Gly-Ala-Leu-Thr-Ser-Gly-Val-His-Thr-Phe-Pro-Ala-Val 176 Leu-Gln-Ser-Ser-Gly-Leu-Tyr-Ser-Leu-Ser-Ser-Val-Val-Thr-Val-Pro-Ser-Ser-Ser-Leu-Gly-Thr-Gln-Thr-Tyr 201 Ile-Cys²⁰²-Asn-Val-Asn-His-Lys-Pro-Ser-Asn-Thr-Lys-Val-Asp-Lys-Arg-Val-Glu-Pro-Lys-Ser-Pro-Lys-Ser²²⁴-Cys²²⁵

226 Asp-Lys-Thr-His-Thr-Cys²³¹-Pro-Pro-Cys²³⁴-Pro-Ala-Pro-Glu-Leu-Leu-Gly-Gly-Pro-Ser-Val-Phe-Leu-Phe-Pro-Pro

251 Lys-Pro-Lys-Asp-Thr-Leu-Met-Ile-Ser-Arg-Thr-Pro-Glu-Val-Thr-Cys²⁶⁶-Val-Val-Val-Asp-Val-Ser-His-Glu-Asp

276 Pro-Glu-Val-Lys-Phe-Asn-Trp-Tyr-Val-Asp-Gly-Val-Glu-Val-His-Asn-Ala-Lys-Thr-Lys-Pro-Arg-Glu-Glu-Gln

301 Tyr-Asn³⁰²-Ser-Thr-Tyr-Arg-Val-Val-Ser-Val-Leu-Thr-Val-Leu-His-Gln-Asp-Trp-Leu-Asn-Gly-Lys-Glu-Tyr-Lys

326 Cys³²⁶-Lys-Val-Ser-Asn-Lys-Ala-Leu-Pro-Ala-Pro-Ile-Glu-Lys-Thr-Ile-Ser-Lys-Alalys-Gly-Gln-Pro-Arg-Glu 351 Pro-Gln-Val-Tyr-Thr-Leu-Pro-Pro-Ser-Arg-Asp³⁶¹-Glu-Leu³⁶³-Thr-Lys-Asn-Gln-Val-Ser-Leu-Thr-Cys³⁷²-Leu-Val-Lys 376 Gly-Phe-Tyr-Pro-Ser-Asp-Ile-Ala-Val-Glu-Trp-Glu-Ser-Asn-Gly-Gln-Pro-Glu-Asn-Asn-Tyr-Lys-Thr-Thr-Pro 401 Pro-Val-Leu-Asp-Ser-Asp-Gly-Ser-Phe-Phe-Leu-Tyr-Ser-Lys-Leu-Thr-Val-Asp-Lys-Ser-Arg-Trp-Gln-Gln-Gly 426 Asn-Val-Phe-Ser-Cys⁴³⁰-Ser-Val-Met-His-Glu-Ala-Leu-His-Asn-His-Tyr-Thr-Gln-Lys-Ser-Leu-Ser-Leu-Ser-Pro 451 Gly-Lys

TABLE 3

Physicochemical and biological properties of LR004

| Property | Analytical Method | Result |
| --- | --- | --- |
| Molecular Weight | Mass Spectrometry | LC: 23718 Da (alkylated)<br>HC: 53037 Da (alkylated G0F/G0F) |
| N-terminal Sequence | Edman Degradation | ⁱ⁾HC: (Q)VQLKQSGPGLVQPS<br>(SEQ ID NO: 3)<br>LC: DILLTQSPVILSVSP<br>(SEQ ID NO: 4) |

TABLE 3-continued

Physicochemical and biological properties of LR004

| Property | Analytical Method | Result |
| --- | --- | --- |
| Glycoform Structures | Waters Q-TOF | G0F/G0F, G0F/G1F, G1F/G1F, G1F/G2F, G1F/G1F-SA[ii)], G1F/G2F-SA[ii)], |
| Melting Point | DSC | 88.84° C.[iii)] |
| pI | IEF | 7.0-8.6 |
| UV Extinction Coefficient | Pace Equation | 1.652 mL/mg cm |
| Antigen Binding ELISA | ELISA | Binding to EGFR |
| EGFR-Positive Tumor Cell Growth Inhibition | Cell Culture | Inhibiting growth of MDA-MB 468 cells |

[i)]After pyroglutamate aminopeptidase treatment
[ii)]SA: Smile acid, N-acetylneuraminic acid (NANA)
[iii)]Melting point of Erbitux ® is 85.28 °C. in the same formulation buffer (100 mM NaCl, 100 mM Glycine, 0.01% polysorbate 80, 10 mM citric acid, pH 5.5 at concentration of 20 mg ± 10 mg/mL)
IEF: isoelectric focusing
pI: isoelectric point
UV: ultraviolet
ELISA: enzyme-linked immunosorbent assay
DSC: differential scanning calorimetry In one aspect, the present disclosure provides an antibody for the treatment of EGFR-expressing cancers, and compositions comprising the same. In some embodiments, the antibody is LR004. In some embodiments, the antibody is LR004 conjugated to an additional agent. In some embodiments, the additional agent comprises a detectable marker or a therapeutic agent. In some embodiments, the detectable marker includes, but is not limited to a fluorescent marker or a radioactive marker. In some embodiments, the therapeutic agent comprises a chemotherapeutic agent, such as a cancer therapeutic.

In general, therapeutic moieties can be conjugated to the LR004 antibody by any suitable technique, with appropriate consideration of the need for pharmokinetic stability and reduced overall toxicity to the subject. A therapeutic, cytotoxic, or labelling/imaging agent (i.e., a "moiety") can be coupled to the antibody either directly or indirectly (e.g., via a linker group). A direct reaction between a moiety and the LR004 antibody is possible when each possesses a functional group capable of reacting with the other. For example, a nucleophilic group, such as an amino or sulfhydryl group, can be capable of reacting with a carbonyl-containing group, such as an anhydride or an acid halide, or with an alkyl group containing a good leaving group (e.g., a halide). Alternatively, a suitable chemical linker group can be used. A linker group can function as a spacer to distance the LR004 antibody from a moiety in order to avoid interference with binding capabilities. A linker group can also serve to increase the chemical reactivity of a substituent on a moiety or the LR004 antibody, and thus increase the coupling efficiency. An increase in chemical reactivity can also facilitate the use of moieties, or functional groups on moieties, which otherwise would not be possible.

Suitable linkage chemistries include maleimidyl linkers and alkyl halide linkers (which react with a sulfhydryl on the antibody moiety) and succinimidyl linkers (which react with a primary amine on the antibody moiety). Several primary amine and sulfhydryl groups are present on immunoglobulins, and additional groups can be designed into recombinant immunoglobulin molecules. It will be evident to those skilled in the art that a variety of bifunctional or polyfunctional reagents, both homo- and hetero-functional (such as those described in the catalogue of the Pierce Chemical Co., Rockford, Ill.), can be employed as a linker group. Coupling can be affected, e.g., through amino groups, carboxyl groups, sulfhydryl groups or oxidized carbohydrate residues (see, e.g., U.S. Pat. No. 4,671,958).

As an alternative coupling method, a moiety can be coupled to the LR004 antibody through an oxidized carbohydrate group at a glycosylation site, as described in U.S. Pat. Nos. 5,057,313 and 5,156,840. Yet another alternative method of coupling the LR004 antibody to a moiety is by the use of a non-covalent binding pair, such as streptavidin/biotin, or avidin/biotin. In these embodiments, one member of the pair is covalently coupled to the LR004 antibody and the other member of the binding pair is covalently coupled to the moiety.

Where a cytotoxic or therapeutic moiety is more potent when free from the LR004 antibody portion of the immunoconjugates of the present technology, it can be desirable to use a linker group which is cleavable during or upon internalization into a cell, or which is gradually cleavable over time in the extracellular environment. A number of different cleavable linker groups have been described. Examples of the intracellular release of a cytotoxic moiety from these linker groups include, e.g., but are not limited to, cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

In one embodiment, the LR004 antibody is coupled to more than one therapeutic, cytotoxic and/or imaging moiety. By poly-derivatizing the LR004 antibody, several cytotoxic strategies can be simultaneously implemented, the LR004 antibody can be made useful as a contrasting agent for several visualization techniques, or a therapeutic antibody can be labeled for tracking by a visualization technique. In one embodiment, multiple molecules of a cytotoxic moiety are coupled to one LR004 antibody. In one embodiment, the LR004 antibody is coupled to a mixture of at least two moieties selected from the group consisting of: a cytotoxic moiety; therapeutic moiety; and labelling/imaging moiety. That is, more than one type of moiety can be coupled to one LR004 antibody. For instance, a therapeutic moiety, such as a polynucleotide or antisense sequence, can be conjugated to the LR004 antibody in conjunction with a chemotoxic or radiotoxic moiety, to increase the effectiveness of the chemo- or radiotoxic therapy, as well as lowering the required dosage necessary to obtain the desired therapeutic effect. Regardless of the particular embodiment, immunoconjugates with more than one moiety can be prepared in a variety of ways. For example, more than one moiety can be coupled directly to the LR004 antibody, or linkers that provide multiple sites for attachment (e.g., dendrimers) can be used. Alternatively, a carrier with the capacity to hold more than one cytotoxic moiety can be used.

As explained above, the LR004 antibody can bear the moiety(ies) in a variety of ways, including covalent bonding either directly or via a linker group, and non-covalent associations. In one embodiment, the antibody is combined with encapsulation carriers. This is especially useful in chemotoxic therapeutic embodiments, as they can allow the therapeutic compositions to gradually release the LR004 antibody chemotoxic moiety over time while concentrating it in the vicinity of the target cells.

In one embodiment, the LR004 antibody is coupled with a cytotoxic moiety which is a radionuclide. Preferred radionuclides for use as cytotoxic moieties are radionuclides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present technology, as a large body of literature has been accumulated regarding their use. $^{131}$I is particularly preferred, as are other β-radiation emitting nuclides, which have an effective range of several millimeters. $^{123}$I, $^{125}$I, $^{131}$I, or $^{211}$At can be conjugated to the LR004 antibody for use in the compositions and methods utilizing any of several known conjugation reagents, including iodogen, N-succinimidyl 3-[$^{211}$At]astatobenzoate, N-succinimidyl 3-[$^{131}$I]iodobenzoate (SIB), and, N-succinimidyl 5-[$^{131}$I]iodob-3-pyridinecarboxylate (SIPC). Any iodine isotope can be utilized in the recited iodo-reagents. Other radionuclides can be conjugated to the LR004 antibody by suitable chelation agents known to those of skill in the nuclear medicine arts.

In one embodiment, the LR004 antibody is coupled with a chemotoxic moiety. Chemotoxic agents include, but are not limited to, small-molecule drugs such as methotrexate, and pyrimidine and purine analogs. Chemotoxin differentiation inducers include phorbol esters and butyric acid. Chemotoxic moieties can be directly conjugated to the LR004 antibody. In one embodiment, the LR004 antibody is coupled to a cytotoxic moiety via a chemical linker. In another embodiment, a moiety is encapsulated in a carrier, which is, in turn, is coupled to the LR004 antibody.

In one embodiment, the LR004 antibody is coupled with a protein toxin moiety. Preferred toxin proteins for use as cytotoxic moieties, include, e.g., but are not limited to, *Actinomycetes* or *Streptomyces* antibiotics, duocarmycin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin didne, mitoxantrone, mithramycin, actinomycin D, 1-dehydrotestosterone, glucocorticoids, procaine, tetracaine, lidocaine, propranolol, and puromycin and analogs or homologs thereof. Preferred toxin proteins for use as cytotoxic moieties further include ricin, abrin, diphtheria toxin, cholera toxin, gelonin, *Pseudomonas* exotoxin, *Shigella* toxin, pokeweed antiviral protein, and other toxin proteins known in the medicinal biochemistry arts. As these toxin agents can elicit undesirable immune responses in the subject, especially if injected intravascularly, it is preferred that they be encapsulated in a carrier for coupling to the LR004 antibody.

In one embodiment, the LR004 antibody is coupled with an enzymatically active toxin. The enzymatically active toxin can be of bacterial or plant origin, or an enzymatically active fragment ("A chain") of such a toxin. Enzymatically active toxins and fragments thereof useful in the present technology are diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, and enomycin. Conjugates of the LR004 antibody with cytotoxic moieties are made using a variety of bifunctional protein coupling agents. Examples of such reagents are SPDP, IT, bifunctional derivatives of imidoesters such a dimethyl adipimidate HCl, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene. The lysing portion of a toxin can be joined to the Fab fragment of the LR004 antibody.

In one embodiment, the LR004 antibody is coupled with a therapeutic moiety. A therapeutic moiety includes, e.g., but is not limited to, anti-metabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), doxorubicin (adriamycin), cisplatin, bleomycin sulfate, carmustine, chlorambucil, cyclophosphamide hydroxyurea or ricin A, and antimitotic agents (e.g., vincristine and vinblastine).

Techniques for conjugating such therapeutic moiety to the LR004 antibody are well known, see, e.g., Arnon, et al., "Monoclonal Antibodies For Immunotargeting Of Drugs In Cancer Therapy", in Monoclonal Antibodies And Cancer Therapy, Reisfeld, et al. (eds.), pp. 243-56 (Alan R. Liss, Inc. 1985); Hellstrom, et al., "Antibodies For Drug Delivery", in Controlled Drug Delivery (2nd Ed.), Robinson, et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera, et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin, et al. (eds.), pp. 303-16 (Academic Press 1985), and Thorpe, et al., "The Preparation And Cytotoxic Properties Of Antibody-Toxin Conjugates", *Immunol. Rev.*, 62: 119-58 (1982).

In one embodiment, the LR004 antibody is coupled with a label moiety, i.e., detectable group. The particular label or detectable group conjugated to the LR004 antibody is not a critical aspect of the present technology, so long as it does not significantly interfere with the specific binding of the antibody. The detectable group can be any material having a detectable physical or chemical property. Such detectable labels have been well-developed in the field of immunoassays and imaging, in general, most any label useful in such methods can be applied to the present technology. Thus, a label is any composition detectable by spectroscopic, photochemical, biochemical, immunochemical, electrical, optical or chemical means. Useful labels include magnetic beads (e.g., Dynabeads™), fluorescent dyes (e.g., fluorescein isothiocyanate, Texas red, rhodamine, and the like), radiolabels (e.g., $^{3}H$, $^{14}C$, $^{35}S$, $^{125}I$, $^{121}I$, $^{112}In$, $^{99}mTc$), other imaging agents such as microbubbles (for ultrasound imaging), $^{18}F$, $^{11}C$, $^{15}O$, (for Positron emission tomography), $^{99m}TC$, $^{111}In$ (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that described the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals ($6^{th}$ Ed., Molecular Probes, Inc., Eugene Oreg.).

The label can be coupled directly or indirectly to the desired component of an assay according to methods well known in the art. As indicated above, a wide variety of labels can be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, e.g., biotin, thyroxine, and cortisol, it can be used in conjunction with the labeled, naturally-occurring anti-ligands. Alternatively, any haptenic or antigenic compound can be used in combination with the LR004 antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds useful as labelling moieties, include, but are not limited to, e.g., fluorescein and its derivatives, rhodamine and its derivatives, dansyl, umbelliferone, and the like. Chemiluminescent compounds useful as labelling moieties, include, but are not limited to, e.g., luciferin, and 2,3-dihydrophthalazinediones, e.g., luminol For a review of various labeling or signal-producing systems which can be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple colorimetric labels can be detected simply by observing the color associated with the label. Thus, in various dipstick assays, conjugated gold often appears pink, while various conjugated beads appear the color of the bead.

III. Preparation of LR004

LR004 is a recombinant, human/mouse chimeric monoclonal antibody that binds specifically to the N-terminal portion of a human EGFR. The sequence of the LR004 heavy and light chains is given in Table 2. As discussed above, the sequence was modified from the cetuximab sequence published in the Drug Bank (Accession Number: DB00002), incorporating five amino acid changes.

The LR004 antibody may be produced in CHO cells using methods known in the art. Production of the antibody in these cells results in two differences in carbohydrate structure compared to cetuximab, which is produced in SP2/0 cells. In particular, the sialic acid of the LR004 is N-acetyl-neuraminic acid (NANA) as opposed to N-glycolyl-neuraminic acid (NGNA) on cetuximab. NANA is considered to be more human-like than NGNA. In addition, while cetuximab contains a high-level of galactose-α-1,3-galactose which is a potent oligosaccharide immunogen, LR004 contains no detectable amount of such carbohydrate structure. The glycan profile of LR004 is much less immunoreactive than that of cetuximab, causing it to be safer for administration to human subjects. Also, owing to these sequences and post-translational differences, LR004 demonstrates a longer serum half-life than cetuximab in repeat-dosage treatment regimens and increased thermostability.

The recombinant LR004 antibody may be expressed in CHO cells using methods known in the art. In some embodiments, the antibody is expressed using a mammalian expression vector introduced into host CHO cells. In some embodiments, the antibody is expressed from recombinant sequences stably integrated into the host CHO cell genome.

Recombinant polynucleotide constructs encoding the LR004 antibody will typically include an expression control sequence operably-linked to the coding sequences of the antibody. As such, another aspect of the present technology includes vectors containing one or more nucleic acid sequences encoding the LR004 antibody. Methods for producing diverse populations of vectors have been described by Lerner, et al., U.S. Pat. Nos. 6,291,160; 6,680,192.

A nucleic acid encoding the LR004 antibody of the present technology may be expressed in CHO cells using a mammalian expression vector. Examples of mammalian expression vectors include, but are not limited to, pCDM8 (Seed, *Nature* 329: 840, 1987) and pMT2PC (Kaufman, et al., *EMBO J.* 6: 187-195, 1987). For example, commonly used promoters are derived from polyoma, adenovirus 2, cytomegalovirus, and simian virus 40. For suitable expression systems for eukaryotic cells useful for expression of the LR004 antibody. See, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another aspect, the present disclosure provides a CHO cell into which a mammalian expression vector comprising LR004 coding sequences has been introduced. In some embodiments, the LR004 coding sequences are present on a replicable vector separate from the genome of the CHO cell.

In some embodiments, the LR004 coding sequences are stably integrated into the genome of the CHO cell.

Once expressed, the LR004 antibody may be isolated and purified using methods known in the art. The biological activity of the antibody may be determined using methods known in the art and described herein. For example, the biological activity of the antibody may be determined in vitro by assessing the binding specificity of the antibody for EGFR, the capacity of the antibody to inhibit EGFR phosphorylation in vitro or in vivo, and assessing the effect of the antibody on tumor cell proliferation in vitro or in animal models.

IV. Methods of Treatment

In one aspect, the present disclosure provides methods for treating EGFR-expressing cancers comprising administering the LR004 antibody to a subject in need thereof, alone or in combination with one or more additional therapeutic agents. In some embodiments, the one or more therapeutic agents comprises, a protein or peptide, such as, for example, an enzymatically active toxin, or active fragment thereof, such as abrin, ricin A, Pseudomonas exotoxin, or diphtheria toxin; a protein such as tumor necrosis factor or interferon-alpha; or, biological response modifiers such as, e.g., lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

In some embodiments, the therapeutic agent comprises a chemotherapeutic agent, including, but not limited to, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), transitional metal complexes, proteasome inhibitors, anti-metabolites (such as nucleoside analogs), alkylating agents, platinum-based agents, anthracycline antibiotics, topoisomerase inhibitors, macrolides, retinoids (such as all-trans retinoic acids or a derivatives thereof); geldanamycin or a derivative thereof (such as 17-AAG), and other standard chemotherapeutic agents well recognized in the art.

In some embodiments, the chemotherapeutic agent includes one or more of adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof (e.g., taxol, paclitaxel and derivatives thereof, taxotere and derivatives thereof, and the like), topetecan, vinblastine, vincristine, tamoxifen, piposulfan, nab-5404, nab-5800, nab-5801, Irinotecan, HKP, Ortataxel, gemcitabine, Oxaliplatin, Herceptin®, vinorelbine, Doxil®, capecitabine, Alimta®, Avastin®, Velcade®, Tarceva®, Neulasta®, lapatinib, sorafenib, erlotinib, Erbitux®, derivatives thereof, chemotherapeutic agents known in the art, and the like. In some embodiments, the chemotherapeutic agent is a composition comprising nanoparticles comprising a thiocolchicine derivative and a carrier protein (such as albumin).

In some embodiments, the chemotherapeutic agent is an antineoplastic agent including, but is not limited to, carboplatin, Navelbine® (vinorelbine), anthracycline (Doxil®), lapatinib (GW57016), Herceptin®, gemcitabine (Gemzar®), capecitabine (Xeloda®), Alimta®, cisplatin, 5-fluorouracil (5-Fu), epirubicin, cyclophosphamide, Avastin®, Velcade®, etc.

Reference to a chemotherapeutic agent herein applies to the chemotherapeutic agent or its derivatives and accordingly the present technology includes either of these embodiments (agent; agent or derivative(s)). "Derivatives" or "analogs" of a chemotherapeutic agent or other chemical moiety include, but are not limited to, compounds that are structurally similar to the chemotherapeutic agent or moiety or are in the same general chemical class as the chemotherapeutic agent or moiety. In some embodiments, the derivative or analog of the chemotherapeutic agent or moiety retains similar chemical and/or physical property (including, for example, functionality) of the chemotherapeutic agent or moiety.

In one aspect, the present disclosure provides a methods for treating cancer comprising determining whether a subject is hypersensitive to cetuximab or is predisposed to having a hypersensitivity reaction to cetuximab. In some embodiments, the method comprises determining whether anti-cetuximab IgE is present in the serum of the subject. In some embodiments, the method comprises determining whether anti-galactose-α-1,3-galactose (Galα1,3Gal) IgE is present in the serum of the subject. In some embodiments, anti-cetuximab IgE or anti-Galα1,3Gal IgE is measured by ELISA. In some embodiments, anti-cetuximab IgE or anti-Galα1,3Gal IgE is measured using a radioallergosor-bent test. In some embodiments, anti-cetuximab IgE or anti-Galα1,3Gal IgE is measured using ImmunoCAP®.

Detection of anti-cetuximab IgE or anti-Galα1,3Gal IgE by ELISA may be done using protocols known in the art, such as those disclosed in Plum, et al., J. Biol. Chem. 286(50):43103-43111 (2011); Mariotte, et al., mAbs 3(4): 396-401 (2011); and Chung, et al., N. Engl. J. Med. 358 (11):1109-1117 (2008). For example, Galα1,3Gal or cetuximab itself may be used as a coating reagent to provide immobilized determinants for IgE binding. Anti-cetuximab IgE or anti-Galα1,3Gal IgE bound to the immobilized determinants may be detected using IgE-specific secondary antibodies and appropriate means to develop and/or quantify the label.

Patient samples may be compared to positive and negative controls prepared using appropriate sera and/or biochemical reagents. For example, negative controls may be prepared using sera from subjects known to lack cetuximab hypersensitivity, with positive controls prepared using sera from subjects known to have cetuximab hypersensitivity. The definition and grading of cetuximab hypersensitivity may be based on symptoms listed in the National Cancer Institute Common Toxicity Criteria, version 3.11,16, which gives the characteristics of a grade 1 reaction as transient flushing or rash with a fever of less than 38° C. (100.4° F.); those of a grade 2 reaction as rash or flushing, urticaria, and dyspnea with or without a fever of more than 38° C.; those of grade 3 as rash, dyspnea, and hypotension; and those of grade 4 as anaphylaxis.

As known in the art, subjects having serum anti-cetuximab IgE or anti-Galα1,3Gal IgE have a higher incidence of severe hypersensitivity to cetuximab than subjects not having the IgE. Accordingly, a subject's level of anti-cetuximab IgE or anti-Galα1,3Gal IgE may serve as an indicator of whether the subject has had or is predisposed to having severe hypersensitivity to cetuximab, and whether the subject is a candidate for treatment with cetuximab. A level of anti-cetuximab IgE or anti-Galα1,3Gal IgE higher than negative controls indicates that a subject has an elevated risk of cetuximab hypersensitivity as compared to subjects not having a level of anti-cetuximab IgE or anti-Galα1,3Gal IgE higher than negative controls.

In some embodiments, a subject with increased risk of cetuximab hypersensitivity has serum anti-cetuximab IgE or anti-Galα1,3Gal IgE levels at least about 1 to at least about 99 percent higher than a subject not having an increased risk of cetuximab hypersensitivity. In some embodiments, the subject has anti-cetuximab IgE or anti-Galα1,3Gal IgE levels at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99 percent higher than a subject not having an increased risk of cetuximab hypersensitivity.

In some embodiments, a subject with increased risk of cetuximab hypersensitivity has serum anti-cetuximab IgE or anti-Galα1,3Gal IgE levels at least about 1 to at least about 100-fold higher than. In some embodiments, the subject has anti-cetuximab IgE or anti-Galα1,3Gal IgE levels at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99-fold higher than a subject not having an increased risk of cetuximab hypersensitivity.

The LR004 antibody can be incorporated into pharmaceutical compositions suitable for administration to subject in need thereof for the treatment of EGFR-expressing cancers. The pharmaceutical compositions generally comprise the antibody together with a pharmaceutically-acceptable carrier in a form suitable for a particular route of administration. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (see, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the antibody are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the antibody, e.g., $C_{1-6}$ alkyl esters.

Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the antibody, use thereof in the compositions is contemplated. Supplementary active compounds can also be incorporated into the compositions.

Pharmaceutical compositions of the present technology are formulated to be compatible with and indented route of administration, such as, for example, parenteral, topical, intravenous, oral, subcutaneous, intraarterial, intradermal, transdermal, rectal, intracranial, intraperitoneal, intranasal; intramuscular route, or respiratory administration.

In some embodiments, formulations are administered locally, directly in to an affected tissue. In some embodiments, formulations are administered systemically. In some embodiments, formulations are administered as a bolus. In some embodiments, formulations are administered for a time-release delivery.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the antibody in the required amount in an appropriate solvent with one or a combination of ingredients enumerated above, as required, followed by filtered sterilization. Generally, dispersions are prepared by incorporating the antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of the present technology can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the LR004 antibody or antibody conjugate can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the antibody is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the antibody is formulated into ointments, salves, gels, or creams as generally known in the art.

The antibody can also be prepared as pharmaceutical compositions in the form of suppositories (e.g., with conventional suppository bases such as cocoa butter and other glycerides) or retention enemas for rectal delivery.

In one embodiment, antibody is prepared with carriers that will protect the antibody against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of antibody calculated to produce the desired therapeutic effect in association with the required pharmaceutical carrier. The specification for the dosage unit forms of the present technology are dictated by and directly dependent on the unique characteristics of the antibody and the particular therapeutic effect to be achieved, and the limitations inherent in the art of compounding the antibody for the treatment of a subject.

The nucleic acid molecules of the present technology can be inserted into vectors and used as gene therapy vectors. Gene therapy vectors can be delivered to a subject by, e.g., intravenous injection, local administration (see, e.g., U.S. Pat. No. 5,328,470) or by stereotactic injection (see, e.g., Chen, et al., 1994. *Proc. Natl. Acad. Sci. USA* 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

In one aspect, the present disclosure provides a method for in vivo tumor imaging comprising administering to a subject an amount of LR004 antibody conjugated to a detectable label suitable for detection by X-radiography, NMR or ESR. For X-radiography, suitable labels include radioisotopes such as barium or cesium, which emit detectable radiation. Suitable markers for NMR and ESR include those with a detectable characteristic spin, such as deuterium, which can be incorporated or conjugated to the antibody using methods known in the art.

The LR004 antibody which has been labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled LR004 antibody will then preferentially accumulate at the location of cells which contain the specific target polypeptide. For example, in vivo tumor imaging is described in S. W. Burchiel, et al., *Tumor Imaging: The Radiochemical Detection of Cancer* 13 (1982).

The LR004 antibody of the present technology is useful for the treatment of EGFR-expressing cancers, and in particular, for the treatment of EGFR-expressing cancers in subjects unable to pursue treatment with cetuximab. Compositions and methods of the present technology are useful for treating all cancers for EGFR inhibition is useful, including but not limited to bladder, breast, cervix, colon, colorectal, head and neck, kidney, lung, pancreatic, and prostate cancer.

When used in vivo for therapy, the LR004 antibody is administered to the subject in effective amounts (i.e., amounts that have desired therapeutic effect). The dose and dosage regimen will depend upon the degree of EGFR-expressing disease present in the individual, and the characteristics of the particular disease in question. In some embodiments, the antibody is administered repeatedly over the course of days, weeks, months, or years until the desired degree of treatment is obtained.

In some embodiments, the LR004 antibody is administered in conjunction with one or more additional therapeutic agents. In some embodiments, the antibody and additional therapeutic agents display a synergistic effect for the treatment of an EGFR-expressing cancer. That is, the combination of antibody and therapeutic agent results in a greater effect than additive effect with respect to, for example, promoting tumor regression or suppressing tumor growth. IN some embodiments, the synergistic effect allows for administration of a lower dose of the antibody and one or more additional agents than would be effective if either were used alone.

Typically, an effective amount of the compositions of the present technology, sufficient for achieving a therapeutic or prophylactic effect, range from about 0.000001 mg per kilogram body weight per day to about 10,000 mg per kilogram body weight per day. In some embodiments, the dosage ranges are from about 0.0001 mg per kilogram body weight per day to about 100 mg per kilogram body weight per day. In some embodiments the compositions are administered at a dosage range of from about 0.0001 to 100 mg/kg, or about 0.01 to 5 mg/kg per day. For example dosages can be 1 mg/kg body weight or 10 mg/kg body weight per day, or within the range of 1-10 mg/kg per day. In some embodiments, a single dosage of antibody ranges from 0.1-10,000 micrograms per kg body weight. In some embodiments, antibody concentrations in a carrier ranges from 0.2 to 2000 micrograms per delivered milliliter. An illustrative treatment regime entails administration once per every two weeks or once a month or once every 3 to 6 months. Intervals between single dosages can be weekly, monthly or yearly. Intervals can also be irregular as indicated by measuring blood levels of antibody in the subject.

In some methods, dosage is adjusted to achieve a plasma antibody concentration, of 1-1000 µg/ml and in some methods 25-300 µg/ml. Alternatively, a formulation can be administered as a sustained release formulation, in which case less frequent administration is required. Dosage and frequency vary depending on the half-life of the antibody in the subject.

In some embodiments, an effective amount of LR004 antibody will provide therapeutic benefit without causing substantial toxicity to the subject. Toxicity of the antibody can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the antibody described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl, et al., In: *The Pharmacological Basis of Therapeutics*, Ch. 1 (1975).

Also within the scope of the present technology are kits comprising the LR004 antibody for use in treating EGFR-expressing cancers. The kit may contain a formulation of the antibody suitable for a particular route of administration and optionally a means for administering the formulation packaged in a suitable container. The kit can further comprise instructions for using the kit to administer the LR004 antibody.

In some embodiments, the kit comprises a formulation of LR004 antibody together with one or more additional therapeutic agents or a detectable label.

EXAMPLES

The following examples are presented in order to more fully illustrate the preferred embodiments of the present technology. These examples should in no way be construed as limiting the scope of the present technology, as defined by the appended claims.

Example 1. Inhibition of EGFR Phosphorylation

Phosphorylation assays and subsequent ELISA analysis were performed using human lung carcinoma cell line A549 and hypopharyngeal carcinoma cell line FaDu. Cells were stimulated with 750 ng/mL TGFs in the presence of different concentrations of LR004 or Erbitux® for 1 hr on ice. Following stimulation, cells were washed with PBS and lysed with cell lysis buffer for subsequent ELISA analysis. The phosphorylation of EGF receptors EGFR\HER2\HER3 were determined by probing with a HRP-conjugated pTyr-4G10 mAb and detected using ELISA.

Results of these in vitro analyses demonstrated that both LR004 and Erbitux® were able to inhibit the phosphorylation of EGFR to the similar extent at all concentrations tested in both tumor cell lines A549 and FaDu (FIG. 1).

Example 2. LR004-Dependent Cell-Mediated Cytotoxicity

Antibody-dependent cell-mediated cytotoxicity (ADCC) is an important mechanism of action of therapeutic monoclonal antibodies against tumors. The aim of this study was to determine whether LR004 and Erbitux® could mediate ADCC against tumor cells in vitro.

Peripheral blood mononuclear cells (PBMCs) were obtained from healthy donors and used as effector cells. The hypopharyngeal carcinoma cell line, FaDu, was used as target cells. FaDu cells were plated in 96-well format at $5 \times 10^3$ cells/well. LR004 at various concentrations (0.01-10,000 ng/mL) was added in triplicate to the individual wells and effector cells were added at an effector:target cell ratio of 30:1 and incubated at 37° C. for 4 hours, and ADCC was examined using the CytoTox 96 Non-Radioactive Cytotoxicity Assay.

Results are shown in FIG. 2. LR004 induced significant ADCC activity against hypopharyngeal carcinoma FaDu cells. At the effector: target ratio of 30:1 and LR004 concentration of 100 ng/mL, ADCC reached the highest percentage of anti-tumor cytotoxicity. Percentages of ADCC activities by healthy donor PBMC were similar in response to both LR004 and Erbitux® at all concentrations (0.01-10, 000 ng/mL) examined in both LR004 reference control sample (LR004-201307001) and bulk solution (LR004-034-201304002). Furthermore, there was a dose-dependency in LR004 mediated ADCC against tumor cell FaDu, confirming a similar anti-tumor mechanism of action of LR004 and Erbitux®.

The primary pharmacology studies conducted with LR004 include binding studies in cell-free system with soluble human EGFR and EGFR-expressing cells, in vitro anti-tumor activity studies using EGFR-positive cancer cell lines, and in vivo anti-tumor activity in EGFR-positive human tumor xenograft models.

Example 3. LR004 Binding Specificity and Affinity

A. Binding to Immobilized Receptor as Measured by ELISA

The binding specificity of LR004 was evaluated in vitro by ELISA. Purified EGFR, HER2, and HER3 were coated on microplates and then blocked. LR004 reference material (LR004-RS-201307001), three lots of LR004 bulk solution (LR004-034-201304002, LR004-034-201304004, LR004-034-201305005), as well as Erbitux®, and the unrelated antibody control hIgG1, were individually diluted to 2000, 400, 80, 16, 3.2, 0.64 and 0.128 ng/mL and added to wells containing the immobilized antigens. Plates were incubated for 30 minutes at 37° C., and were washed. Binding of LR004 or Erbitux® with immobilized antigens was detected with HRP labeled secondary antibody and TMB substrate.

Figure 3:
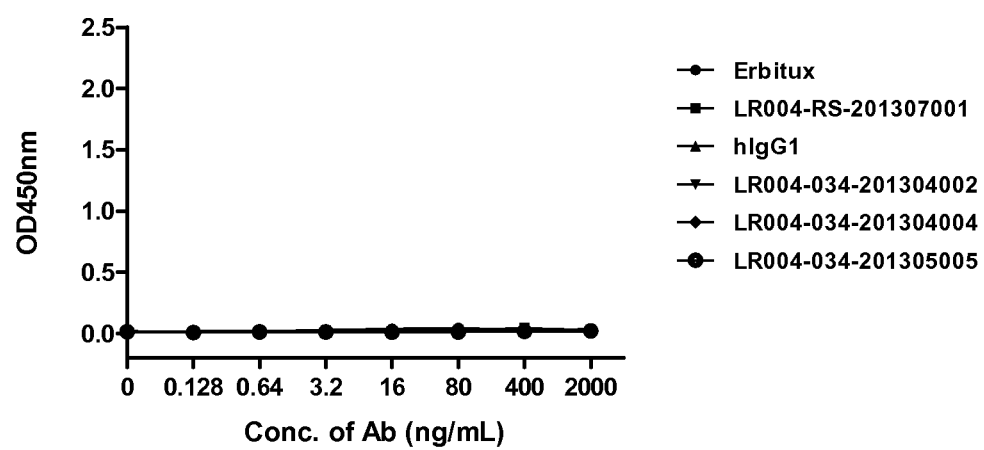
FIG. 3A-C are charts showing the binding specificity of LR004 and Erbitux® as shown by enzyme-linked immunosorbent assay (ELISA).

As shown in FIG. 3, both LR004 and Erbitux® bound only EGFR antigen, and not HER2 or HER3 antigens, suggesting high specificity for the intended EGFR target. LR004 exhibited near identical binding affinity for EGFR to that of Erbitux®.

B. Binding to Soluble EGFR as Measured by BIAcore

The binding affinity of LR004 to sEGFR was determined by surface plasmon resonance (SPR) and ELISA and compared with to that of Erbitux®. In the SPR assay, LR004 or Erbitux® were immobilized to a CMS BIAcore sensor chip, non-cross-linked proteins were removed, and unreacted sites were blocked. Purified recombinant human sEGFR protein at concentrations of 8, 16, 32, 64, and 128 nM were flowed continuously over the sensor surface. The chip surface between runs was regenerated with 10 mM Glycine-HCl (pH 2.5).

Figure 4:
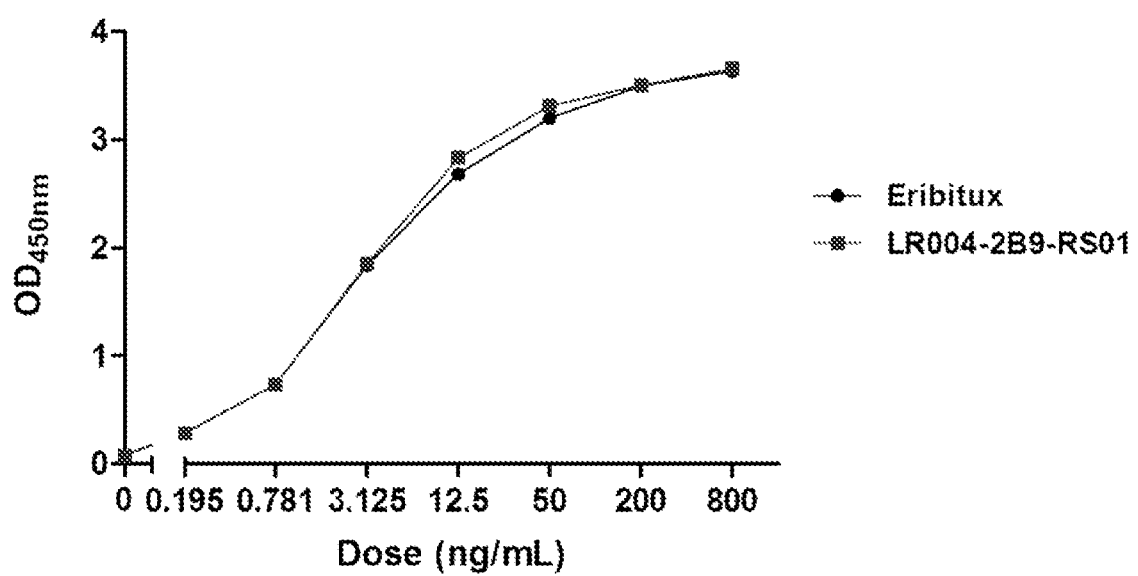
FIG. 4 is a chart showing the binding of LR004 and Erbitux® to soluble EGFR as shown by ELISA.

In the ELISA, sEGFR was again immobilized to the wells of the microplate. LR004 or Erbitux® were diluted and added to the wells coated with sEGFR. After 1 hour incubation at 37° C., the plate was washed. The binding of LR004 or Erbitux® to immobilized sEGFR was detected with HRP labeled anti-human Fc monoclonal antibodies and TMB substrate. The optical density (OD) of each well was determined at wavelength 450 nm. Using this methodology, Kd values of 3.23 and 3.5 nM for LR004 and Erbitux®, respectively (FIG. 4 and Table 4).

Using surface plasmon resonance (SPR/BIAcore), it was found that sEGFR bound to the immobilized LR004 with a Kd value of 2.80 nM, similar to that observed for binding of the Erbitux® (Kd=3.88 nM) (see Table 4 below).

TABLE 4

Binding affinities of LR004 and Erbitux ® to human EGFR

| Method | Receptor form | LR004 | Erbitux ® |
|---|---|---|---|
| | | $K_d$ (nM) | |
| SPR (BIAcore) | soluble receptor | 2.80 | 3.88 |
| | | $EC_{50}$ (ng/mL) | |
| ELISA | Immobilized receptor | 3.23 | 3.50 |

C. Binding Cell Surface EGFRs as Measured by Flow Cytometry

The binding of LR004 to cell surface EGF receptors was evaluated by flow cytometry in nine tumor cell lines with different EGFR expression levels. Commercially available Erbitux® was used as a comparator for these experiments. Cell concentration was adjusted to $2 \times 10^6$ cells/mL and binding assay was performed using $1 \times 10^5$ cells. Two different concentrations (200 ng/mL and 1000 ng/mL) of LR004 or Erbitux® were added to the cells and co-incubated at 4° C. for 1 hour. The cells were washed with phosphate-buffered saline (PBS) and incubated with RPE-conjugated goat anti-human IgG at 4° C. Cells were washed and resuspended in 250 mL PBS for flow cytometric analysis. The geometric mean (G-mean) of fluorescence intensity was recorded and used for data analysis.

Figure 5:
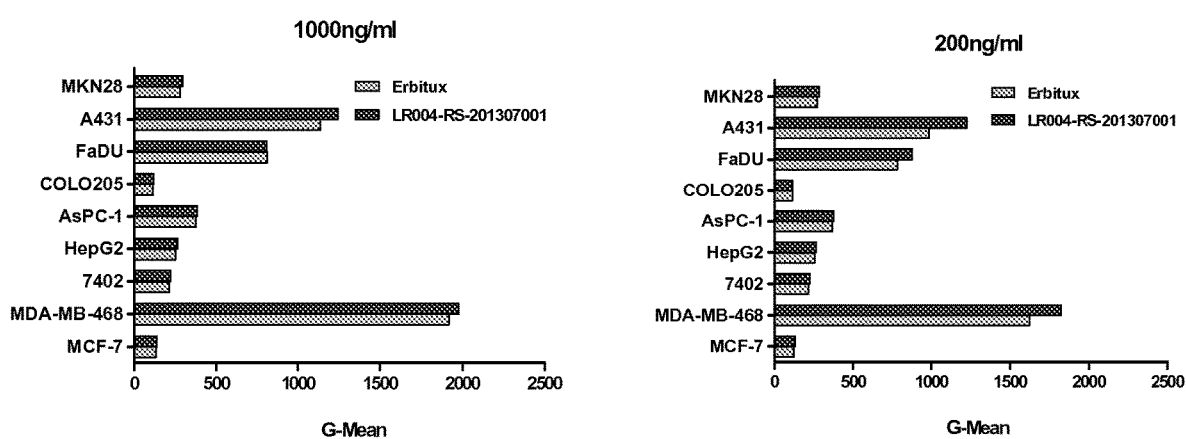
FIG. 5 is a chart showing the binding of LR004 or Erbitux® to cell-Surface EGFR in tumor cell lines.

As shown in FIG. 5, binding of LR004 to EGF receptor was detected in nine different tumor cell lines with variable levels of EGFR expression, including gastric cancer cell line MKN28, epidermoid carcinoma cell line A431, hypopharyngeal carcinoma cell line FaDu, colorectal adenocarcinoma cell line COLO205, pancreas adenocarcinoma cell line AsPC-1, heptacellular carcinoma cell lines HepG2 and 7402, breast carcinoma cell lines MDA-MB-468 and MCF-7. The most notable binding was observed in MDA-MB-468 breast carcinoma cells and in the A431 epidermoid carcinoma line. The binding activity of LR004 to EGFR was similar to that of Erbitux® in all of tumor cell lines examined, suggesting the two antibodies may share the similar structure domain at EGFR binding site.

High-EGFR expression cell lines MDA-MB-468, FaDu and A431 were subsequently used as target cells for LR004 binding study. In the first experiments, LR004 was FITC labelled, and unlabeled Erbitux® was used as competing ligand. In a second series of experiments, Erbitux® was similarly FITC-labelled and LR004 was used as competing ligand. In each case, cell concentrations were adjusted to $2 \times 10^6$ cells/mL and binding assays were performed in $1 \times 10^5$ cells. Equal volumes of FITC-conjugated LR004 were mixed with different concentrations of Erbitux® or human IgG1 mAb (80, 16, 3.2, 0.64, 0.128, and 0 μg/mL) and added to the high-EGFR expression target cells. After incubation for 1 hr on ice, the cells were washed with cold PBS containing 0.2% BSA. Cells were washed and resuspended in 250 μL PBS for flow cytometric analysis.

Figure 6:
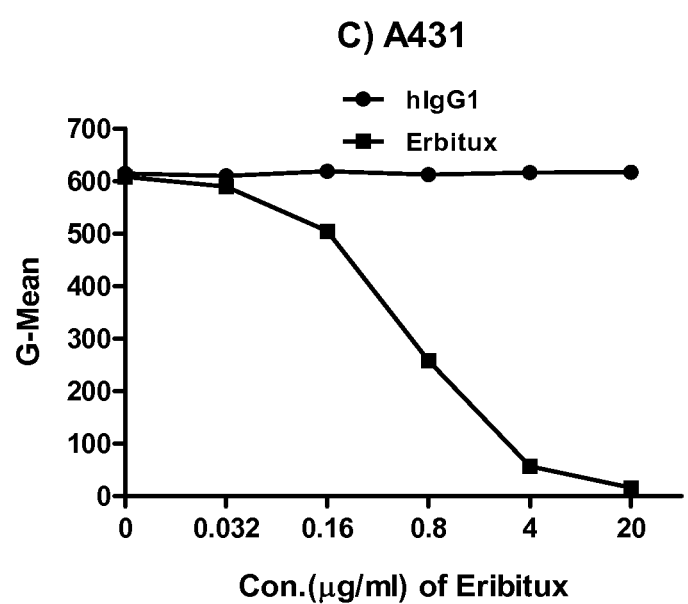
FIG. 6A-C are charts showing the inhibition of FITC-labelled LR004 binding in EGFR-expressing cell Lines by Erbitux®.

As shown in FIG. 6, Erbitux® was shown to compete with LR004 for the binding to EGFR-expressing cell lines. The binding of LR004 to target cell surface EGF receptor was abrogated by Erbitux® in a dose-dependent manner High dose treatment (20 μg/mL) almost completely blocked FITC-conjugated LR004 binding. In contrast, control mAbs (human IgG1) could not block the binding of LR004 with EGF receptors, suggesting that LR004 may recognize the similar ligand-binding epitope of EGF receptors with Erbitux®. The $IC_{50}$ values calculated for the inhibition of LR004 binding by Erbitux® were shown in Table 5.

TABLE 5

Inhibition of FITC-Labelled LR004 by Erbitux ® in Three Cancer Cell Lines

| Cell Line | $IC_{20}$ (µg/mL) | $IC_{50}$ (µg/mL) | $IC_{80}$ (µg/mL) |
|---|---|---|---|
| FaDu | 0.04 | 0.12 | 0.40 |
| A431 | 0.19 | 0.61 | 1.91 |
| MDA-MB-468 | 0.17 | 0.44 | 1.15 |

Using a different approach, MDA-MB-468 was selected as the target cell line for the inhibition of labelled Erbitux® binding by LR004. Binding assays were performed in $1 \times 10^5$ tumor cells. FITC-conjugated Erbitux® was mixed with different concentrations of LR004 or human IgG1 mAb (80, 16, 3.2, 0.64, 0.128, and 0 µg/mL) and added to MDA-MB-468 cells. After incubation for 1 hr on ice, cells were washed with cold PBS containing 0.2% BSA. Cells were resuspended and analyzed by flow cytometric analysis.

Figure 7:
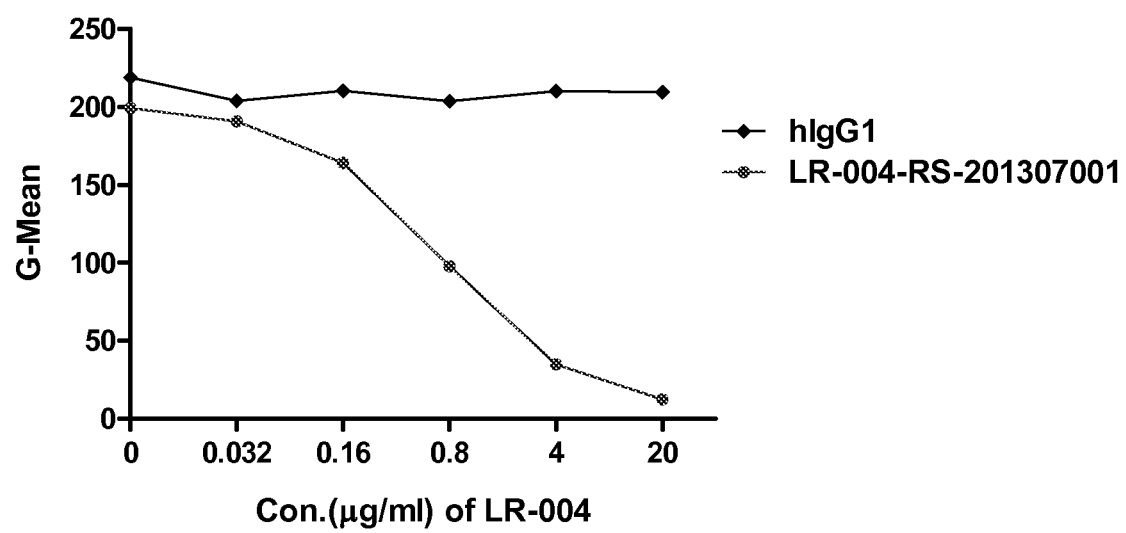
FIG. 7 is a chart showing the inhibition of FITC-labelled Erbitux® binding by LR004 (LR-004) in MDA-MB-468 cancer cells.
Figure 9:
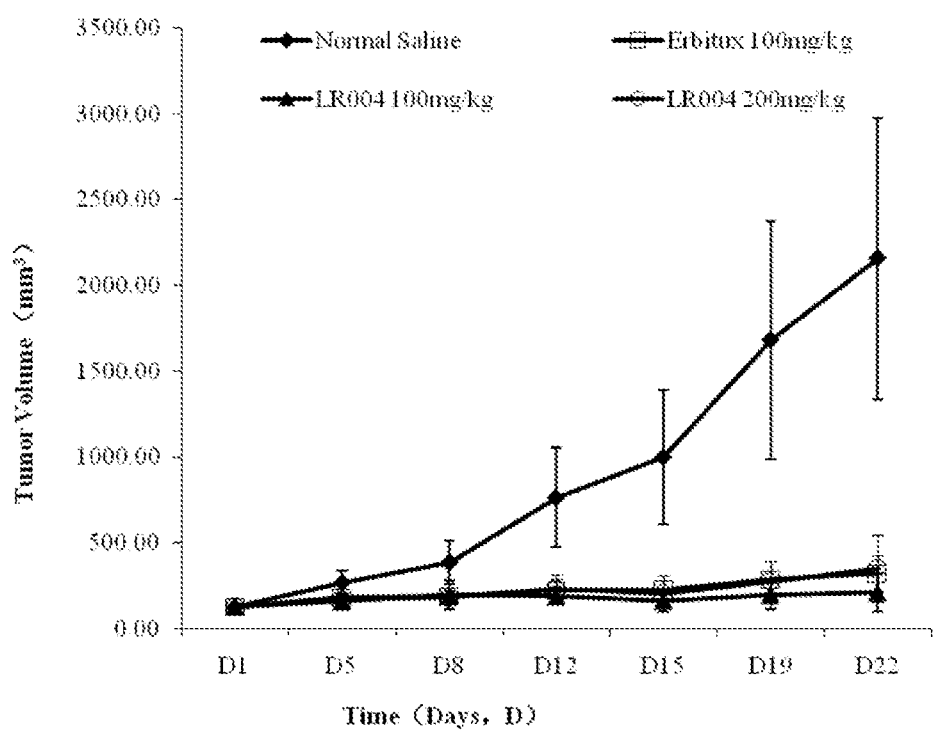
FIG. 9 is a chart showing the effect of high-dose LR004 or Erbitux® on GEO tumor growth in BALB/c nude mice. Data represent the average on the total mice for each group; bars, SD. (N=5/group).

As shown in FIG. 7, LR004 was shown to compete with Erbitux® for the binding of MDA-MB-468. The binding of Erbitux® to target cell surface EGF receptors was abrogated by LR004 in a dose-dependent manner. High dose treatment (20 µg/mL) almost completely blocked FITC-conjugated LR004 to receptors. In contrast, control mAbs (human IgG1) could not block the binding of LR004 with EGF receptors. The results in this study were comparable to those observed in the previous experiments with labelled LR004, suggesting that LR004 and Erbitux® recognize the same ligand-binding epitope of EGF receptor.

Example 4. LR004 In Vitro Anti-Tumor Activity

The antitumor activity of LR004 was also examined directly in vitro. Four human cancer cell lines, including breast cancer cell MDA-MB-468, colon cancer cell LoVo, hypopharyngeal carcinoma cell FaDu, and epidermoid carcinoma cell A431, were tested in this study.

MDA-MB-468 and LoVo were used in the first study. Each cell line (5,000 cells) was incubated overnight. Culture supernatant from the tumor cell lines was discarded and different concentration of LR004 or Erbitux® were added. After incubation for 48 hours at 37° C., 20 µL of CCK-8 mixed substrate were added to each well and incubated for 3 hours at 37° C. The OD450 nm was determined using a microplate reader.

In another experiment, FaDu and A431 (5,000 cells) was incubated with different concentration of LR004 or Erbitux® in a 96-well flat-bottomed plate in triplicate. After incubation for 96 hr at 37° C., substrate was added to each well and incubated for 10 minutes in darkness. The RLU (relative chemiluminescence units) was determined using a chemiluminescence method. The inhibition ratio (IR) was calculated as follows: IR (%)=[RLU value of untreated cells −RLU value from treated cells]/(RLU value of untreated cells)

Results are shown in FIG. 8. MDA-MB-468 was the most sensitive cell line to the antibodies in the four selected cell lines and the reaction of A431 and FaDu was weaker. Both antibodies were capable of inhibiting the proliferation of each cell to the similar extent, suggesting that LR004 has the similar in vitro antitumor activity to Erbitux®.

Example 5. LR004 In Vivo Anti-Tumor Activity

BALB/c nude mice were used for human tumor xenograft studies with LR004 and Erbitux®. A small group of five mice was used for establishment of tumor-bearing mice. Although Human colon cancer cell line GEO, and human lung cancer cell line A549 were both used for the xenograft model development, only results with the GEO line are presented here. Tumor cells were injected s.c. into the right posterior flank of nude mice. When the tumors had reached a volume of 400-600 mm³, tumor-bearing mice with good tumor and health condition were selected. Tumors were removed and cut into small pieces of 2-3 mm3 in size and inoculated s.c. into the right posterior flank of the nude mice. When the tumor volumes grew to 100-300 mm³, mice were randomly allocated to control, low, medium and high dose groups of LR004 or Erbitux® at 10 mice/group. Mice were dosed i.v., twice weekly. Tumor dimensions were measured twice weekly with calipers, and tumor weight after euthanasia was measured and the tumor weight inhibition rate was calculated for each group. The results are considered to be negative if the rate was ≤60% and positive if it was >60%.

Figure 10:
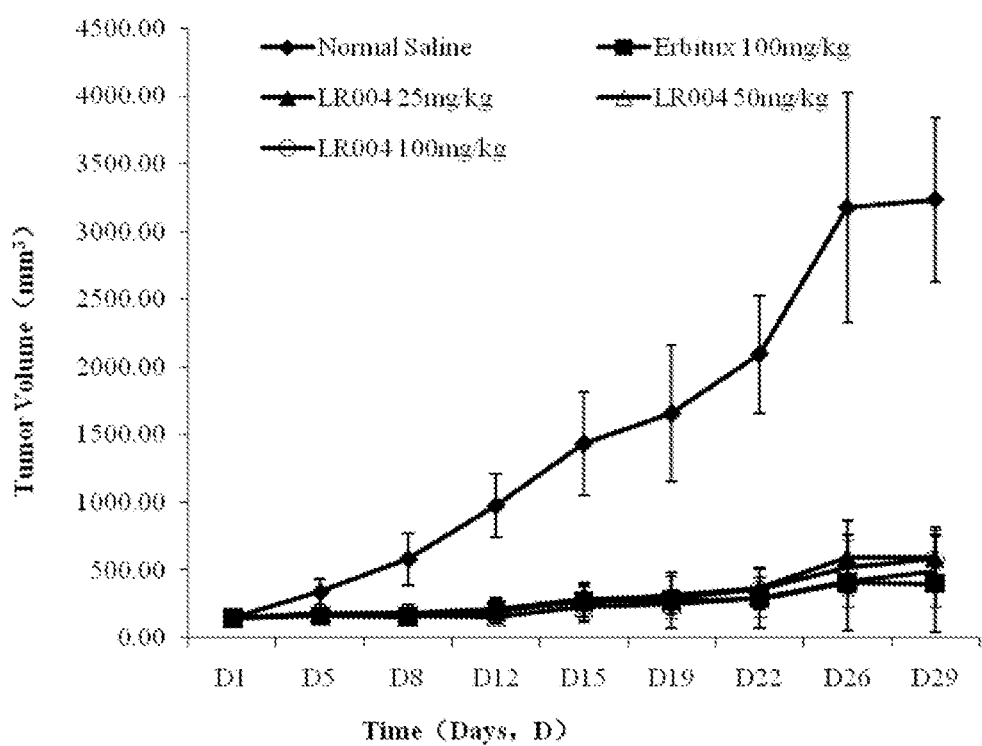
FIG. 10 is a chart showing the effect of LR004 dose-response on GEO tumor growth in BALB/c nude mice in vivo. Data represent the average on the total mice for each group; bars, SD. (N=8/group).

FIG. 10 shows the in vivo antitumor effect of high doses (100-200 mg/kg LR004) and 100 mg/kg Erbitux® on established GEO human colon carcinoma xenograft. Mice were dosed twice weekly for three weeks.

In the next experiment a dose-response was performed with LR004 and a high dose of Erbitux® was again used as control. In this experiment, mice received injections of 100 mg/kg/dose Erbitux® or 25, 50 or 100 mg/kg/dose LR004, twice weekly for four weeks. Each group consisted of 8 mice.

Results are shown in FIG. 10. LR004 and Erbitux® both reduced the tumor volume significantly in both studies. The second experiment was repeated again with very similar results and complete tumor suppression by all doses of LR004 and Erbitux®. There was no significant difference between the two antibodies or between the different doses of LR004 used in these experiments.

Example 6. LR004 Pharmacodynamics

In addition to these initial completed in vitro and in vivo pharmacology studies, the efficacy of LR004 against several other different EGRF-expressing tumor types, including SW948 colorectal adenocarcinoma, A431 epidermoid carcinoma and MDA-MB-468 breast carcinoma tumor lines, will be assessed as shown in Table 6 and Table 7.

TABLE 6

EGFR-Expressing Tumor Types Evaluated in Mouse Xenograft Model In vivo

| | |
|---|---|
| GEO Colon Cancer | SW948 Colorectal Adenocarcinoma |
| A431 Epidermoid Carcinoma | MDA-MB-468 Breast Carcinoma |

Studies with GEO, SW948 and A4331 tumor lines will be performed in BALB/c nude mice and (MDA-MB-468 tumors will be evaluated in NOD SCID mice). Solid tumors will initially be grown in vivo in small groups of BALB/c nude mice. When tumors grow to 400-600 mm³, tumors will be excised and cut into small pieces of 2-3 mm³, and inoculated s.c. into small groups of mice. When tumors grow to 100-300 mm³, mice will be randomized and mice will be dosed i.v. twice weekly for 4 weeks with vehicle, Erbitux® (dose TBD) or a low, mid or high dose of LR004. Mice will be observed for up to 4 weeks following tumor cell implantation and tumor volume will be measured and calculated. Tumor weight will be measured after terminal sacrifice and the inhibition rate or effect will be calculated for each treatment group relative to control. The results will be considered to be negative if the rate is ≤60%, and will be considered to be positive if it is >60%. The overall design for the main studies with these cell lines is presented below.

TABLE 7

In vivo Pharmacodynamic Tumor Xenograft Studies with LR004

| Group | Treatment | Dose (mg/kg) | Treatment Regimen | Number of Males |
|---|---|---|---|---|
| 1 | Vehicle | 0 | Twice weekly for 4 weeks | 10 |
| 2 | Erbitux® | TBD | | 10 |
| 3 | LR004 | TBD (low) | | 10 |
| 4 | LR004 | TBD (mid) | | 10 |
| 5 | LR004 | TBD (high) | | 10 |

Each study of 50 mice with these four tumor type will be repeated once for N=2 for each tumor type. Prior to each main stud with groups of 10 males, a smaller pilot study will be performed with both LR004 and Erbitux® using groups of 5 male mice, and both a low and high dose of LR004 and known efficacious dose of Erbitux®. The results of these definitive efficacy studies will be used for determining the dose range for subsequent repeat-dose safety studies of LR004.

Example 7: Pharmacology

A. Pharmacokinetics of LR004 in Cynomolgus Monkeys

A pilot pharmacokinetic (PK) study was performed in small groups of male Cynomolgus monkeys as shown in Table 8. Two male monkeys were dosed with 18 mg/kg LR004 as a 1 hr IV infusion. A second group of two monkeys was dosed similarly with 18 mg/kg Erbitux® as described in Table 8 below. Blood samples were collected at the indicated time points out to 24 days (577 hr) post-dose, and serum samples were prepared and analyzed for LR004 or Erbitux® concentration by a validated ELISA as described above.

TABLE 8

Pilot Pharmacokinetic Study of LR004 and Erbitux® in Monkeys

| Group | Treatment | Dose level (mg/kg) | Dose Administration | Blood Sampling Time points (hr) | Number of Males |
|---|---|---|---|---|---|
| 1 | LR004 | 18.0 | IV infusion over 60 minutes | Pre-dose, 0.33, 0.67, 1, 2, 3, 5, 9, 13, 25, 49, 97, 145, 193, 241, 289, 337, 385, 433, 481, 529, 577 | 2 |
| 2 | Erbitux® | 18.0 | | | 2 |

Figure 11:
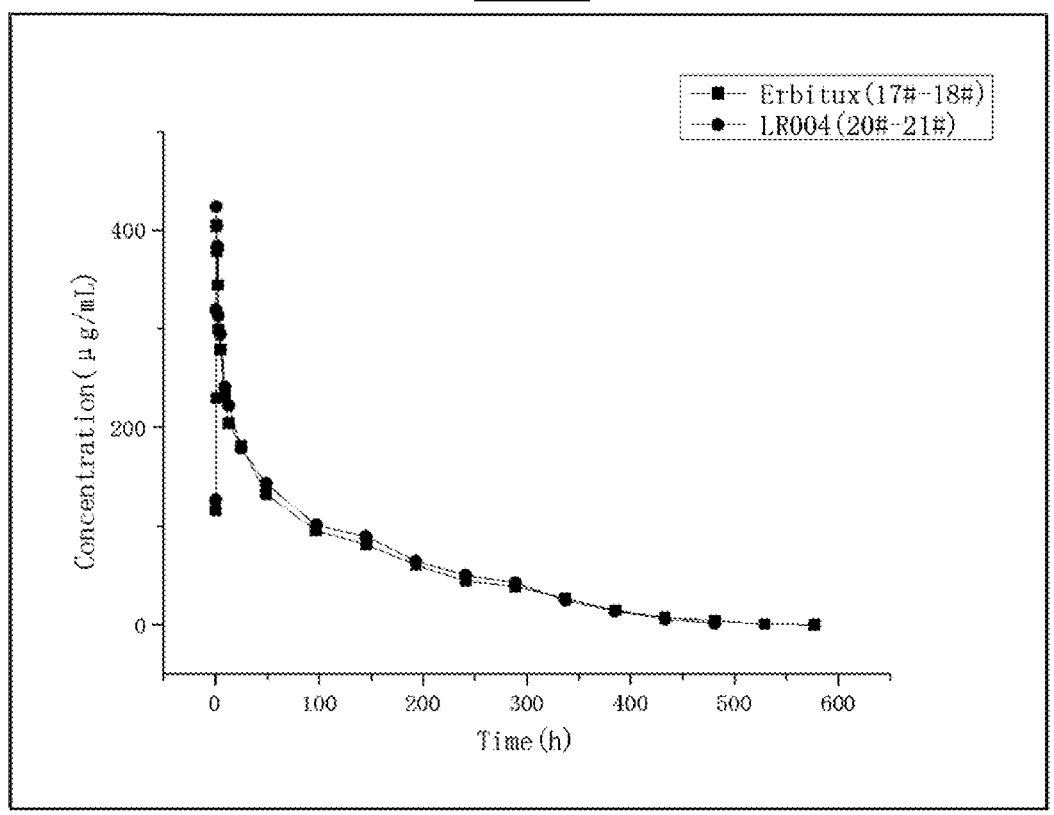
FIG. 11 is a chart showing the concentration-time profile for LR004 and Erbitux® following IV administration to cynomolgus monkeys (18 mg/kg).

The kinetics of LR004 and Erbitux® were nearly identical following single dose IV infusion at 18 mg/mL in male Cynomolgus monkeys. The $C_{max}$ values ranged from 403-423 for Erbitux® and LR004, respectively, with a $T_{max}$ of 1 hr corresponding to the end of the 1 hr infusion. Exposure, as assessed by AUC levels were virtually identical (30-32 mg·hr/L). Half-life values were also highly similar and were 133-137 hr for Erbitux® and LR004, respectively. As shown in FIG. 11 and Table 9, LR004 exhibited kinetics consistent with those already established for the marketed Erbitux® product.

TABLE 9

Pharmacokinetic Parameters of LR004 and Erbitux® Following 1 hr IV Infusion

| Parameter | Erbitux® | LR004 |
|---|---|---|
| $C_{max}$ (ng·mL$^{-1}$) | 403.24 | 423.82 |
| $T_{max}$ (h) | 1.00 | 1.00 |
| $AUC_{(0-\infty)}$ (mg·h·L$^{-1}$) | 30.45 | 31.91 |
| MRT$^a$ (h) | 126.50 | 123.97 |
| CL (mL·h$^{-1}$·kg$^{-1}$) | 0.64 | 0.56 |
| Vd (mL·kg$^{-1}$) | 121.11 | 109.97 |
| $t_{1/2}$ (h) | 133.14 | 137.08 |

$^a$MRT: Mean Residence Time (hours)

B. Pharmacokinetics of LR004 in Monkeys with Single and Repeated IV Dosing

Groups of six Cynomolgus monkeys per sex were treated with either a single 18 mg/kg dose of Erbitux® or repeated IV doses of Erbitux® on Days 1, 21, 28 and 35, or Single doses of LR004 of 6, 18 or 54 mg/kg or repeated IV doses of 18 mg/kg LR004 on days 1, 21 and 35 as shown in Table 10. Blood samples were collected and serum samples prepared from each animal prior to dosing and at 0.33, 0.67 1, 2, 3, 5, 9, 13, 25, 49, 97, 145, 193, 241 hours (10 days) for monkeys dosed at 6 mg/kg, for up to 18 days following dosing with 18 mg/kg, for up to 28 days for dosing at 54 mg/kg. For monkeys dosed repeatedly with either LR004 or Erbitux® at 18 mg/kg, blood samples were collected for up to 22 days (529 hours) following the final dose on day 35, as presented in Table 10. Serum samples were assayed for concentrations of LR004 or Erbitux® using a validated ELISA method.

TABLE 10

Design of Single and Repeated IV Dose PK/TK Study of LR004
and Erbitux ® in Cynomolgus Monkeys

| Group | Treatment | Dose Level (mg/kg) | Dose Regimen | Blood Collection Time points (hr) (post final dose) | Number of Monkeys per sex |
|---|---|---|---|---|---|
| 1 | Erbitux ® | 18 | Single Dose | 0-432 hr | 3 |
| 2 | Erbitux ® | 18 | Days 1, 21, 28, 35 | 0-529 hr | 3 |
| 3 | LR004 | 6 | Single Dose | 0-240 hr | 3 |
| 4 | LR004 | 18 | Single Dose | 0-432 hr | 3 |
| 5 | LR004 | 18 | Days 1, 21, 28, 35 | 0-529 hr | 3 |
| 6 | LR004 | 54 | Single Dose | 0-672 hr | 3 |

Figure 12:
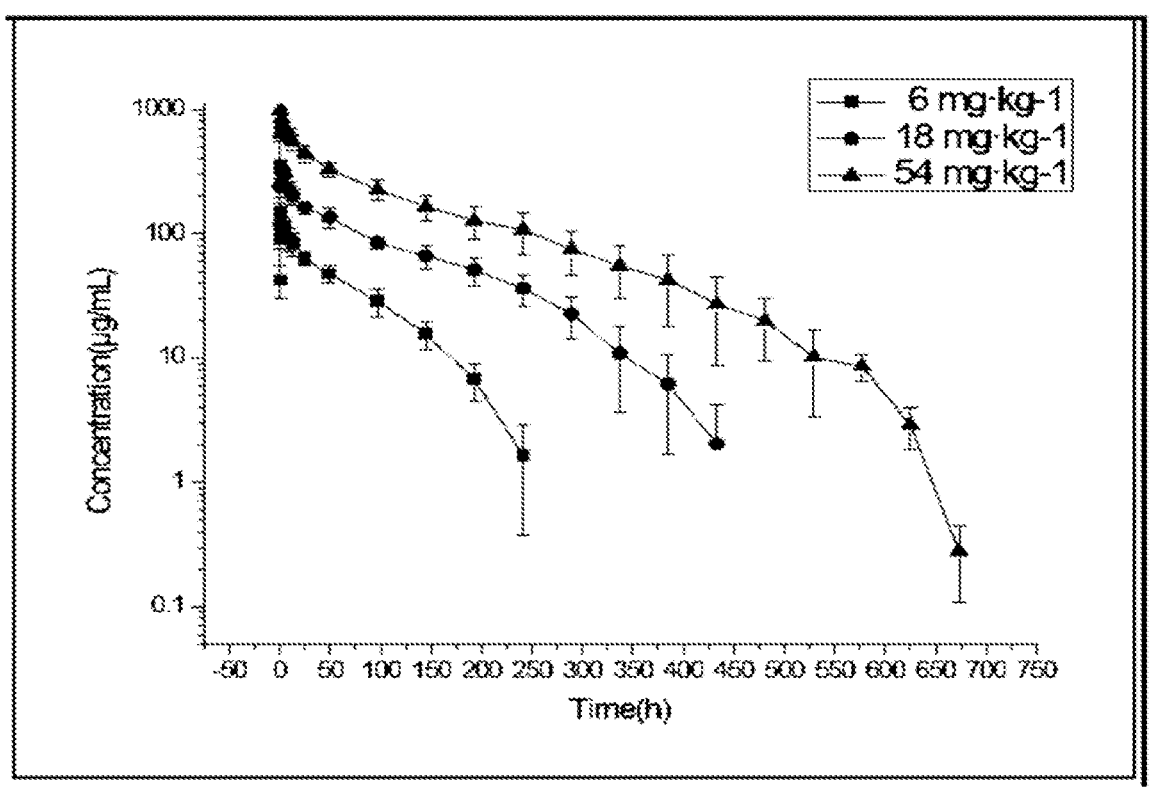
FIG. 12 is a chart showing serum LR004 concentrations following IV dosing in cynomolgus monkeys.

Following single dose IV administration of LR004 to male and female Cynomolgus monkeys at 6, 18 or 54 mg/kg, dose-dependent serum exposure and first-order serum kinetics were observed for this antibody (FIG. 12). Maximum serum concentration ($C_{max}$) ranged from 148 μg/mL to 992 μg/mL for the 6 and 54 mg/kg dose levels, respectively. The observed $T_{max}$ was approximately 1 hour at all three dose levels, and half-life of LR004 determine in this experiment increased with dose and ranged from 51 hr at 6 mg/kg to 98 hr at 18 mg/kg to 116 hr at 54 mg/kg (Table 11). Overall exposure, as determined by AUC values was, however, relatively dose proportional and clearance was relatively consistent and ranged from 0.7-0.8 mL/hr·kg. These parameters observed for the 18 mg/kg dose level were consistent with those determined for Erbitux® at this same dose level in Cynomolgus monkeys.

TABLE 11

Pharmacokinetic Parameters for Single IV Dose
Administration of LR004 to Cynomolgus Monkeys

| Parameters | 6 mg/kg Mean | SD[a] | 18 mg/kg Mean | SD | 54 mg/kg Mean | SD |
|---|---|---|---|---|---|---|
| $C_{max}$(μg · mL$^{-1}$) | 148.27 ± | 25.31 | 352.71 ± | 40.4 | 992.19 ± | 42.7 |
| $T_{max}$(h) | 1.00 ± | 0 | 1.00 ± | 0 | 1.17 ± | 0.41 |
| $AUC_{(0-\infty)}$(mg · h · L$^{-1}$) | 7119.72 ± | 1362.6 | 25191.70 ± | 4574 | 72902.56 ± | 16371.12 |
| MRT(h)[b] | 60.35 ± | 4.19 | 102.89 ± | 9.68 | 126.03 ± | 23.73 |
| CL(mL · h$^{-1}$ · kg$^{-1}$) | 0.85 ± | 0.17 | 0.71 ± | 0.12 | 0.78 ± | 0.22 |
| Vd(mL · kg$^{-1}$) | 61.97 ± | 9.75 | 99.20 ± | 9.81 | 124.72 ± | 9.49 |
| $t_{1/2}$(h) | 51.16 ± | 8.06 | 98.51 ± | 13.59 | 116.44 ± | 25.3 |

[a]SD: Standard Deviation
[b]MRT: Mean Residence Time (hours)

Figure 13:
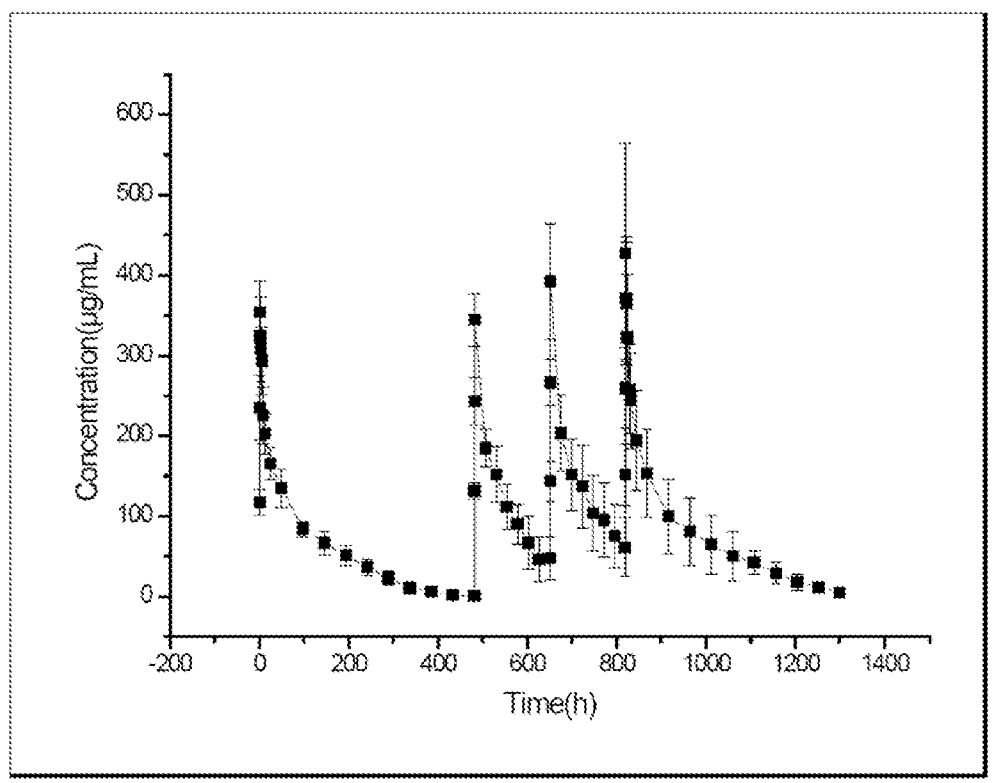
FIG. 13 is a chart showing serum concentrations of LR004 in cynomolgus monkeys following IV dosing with 18 mg/kg on days 1, 21, 28, and 35.

With repeated dosing of both LR004 and Erbitux® at 18 mg/kg (4 doses on days 1, 21, 28 and 35), both antibodies exhibited consistent kinetics and did not exhibit significant accumulation over time, despite slightly higher peak serum levels (for LR004) immediately post-dose on days 21, 28 and 35 (FIG. 13).

These serum levels were not appreciably different from those observed following IV dosing with 18 mg/kg Erbitux®. Comparison of kinetics of both compounds after the 1st dose showed only slightly greater Volume of distribution ($V_D$) for LR004 relative to Erbitux® and slightly lower Cmax and $AUC_{(0-\infty)}$. By the 4th dose however, $C_{max}$ and AUC values were comparable between the two products, although LR004 showed a much higher $V_D$ and longer half-life compared to Erbitux® following the 4th dose. Pharmacokinetic parameters for the first and last (4th) doses of LR004 or Erbitux® in this study are presented in Table 12 below.

TABLE 12

PK Parameters for LR004 and Erbitux ® for First and
Last (4th) IV Dose at 18 mg/kg in Cynomolgus Monkeys

| Parameters | First dosing LR004 | Erbitux ® | Last (4th) dosing LR004 | Erbitux ® |
|---|---|---|---|---|
| $C_{max}$(μg · mL$^{-1}$) | 352.71 | 455.21 | 428.00 | 435.09 |
| $T_{max}$ (h) | 1.00 | 1.00 | 1.00 | 1.17 |
| $AUC_{(0-\infty)}$(mg · h · L$^{-1}$) | 25191.70 | 29738.36 | 32636.20 | 28908.05 |
| MRT(h)[a] | 102.89 | 99.90 | 109.39 | 82.91 |
| CL (mL · h$^{-1}$ · kg$^{-1}$) | 0.71 | 0.60 | 0.74 | 0.74 |
| Vd (mL · kg$^{-1}$) | 99.20 | 80.80 | 92.01 | 59.10 |
| $t_{1/2}$ (h) | 98.51 | 93.92 | 110.91 | 70.17 |

[a]MRT: Mean Residence Time (hours)

Example 8: LR004 Carbohydrate Structure

A. Reversed-Phase High Performance Liquid Chromatography

Acid hydrolysis of LR004 and Erbitux® was performed using 11.5% (v/v) acetic acid and incubated at 80° C. for 60 minutes. Sialic acid standards were prepared in Milli Q $H_2O$ from a stock solution containing 0.619 mg/mL NANA and 0.651 mg/mL NGNA. The DMB (4,5-methylenedioxy-1,2-phenylenediamine dihydrochloride) labeling reactions were performed in triplicate for each sample. Labeling reactions were performed at 55° C. for 3 h by combining 10 or 40 μL (0.3-0.6 μg, depending on protein concentration) of acid-hydrolyzed protein with 200 μL DMB labeling solution (7 mM DMB, 1.4 M acetic acid, 0.75 M Beta-mercaptoethanol, and 18 mM Sodium dithionite). Reactions were quenched by aliquoting 50 μL into 1 mL of Milli Q $H_2O$ and vortexing. Depending on the protein concentration, 25-100 μL (3-9 ng)

was injected for reversed-phase high performance liquid chromatography (RP-HPLC) analysis.

RP-HPLC was performed using Xbridge HPLC column, 3.0 mm×100 mm, 3.5 μm with a 0.5 μm pre-column filter. The fluorescence detector was configured for excitation at 373 nm and emission at 448 nm. The column temperature was 30° C., and the autosampler was set to 4° C. Mobile phase A was 7% Methanol/93% MilliQ $H_2O$ (v/v) and B was 7% Methanol/50% Acetonitrile/43% MilliQ $H_2O$, and the flow rate was 0.4 mL/min with the gradient shown in Table 13.

TABLE 13

RP-HPLC Gradient for LR004 Sialic Acid Analysis

| Time (minutes) | % B |
| --- | --- |
| 0 | 9 |
| 3 | 9 |
| 6 | 12 |
| 12 | 15 |
| 20 | 40 |
| 23 | 100 |
| 24 | 100 |
| 25 | 9 |
| 30 | 9 |

Figure 14A:
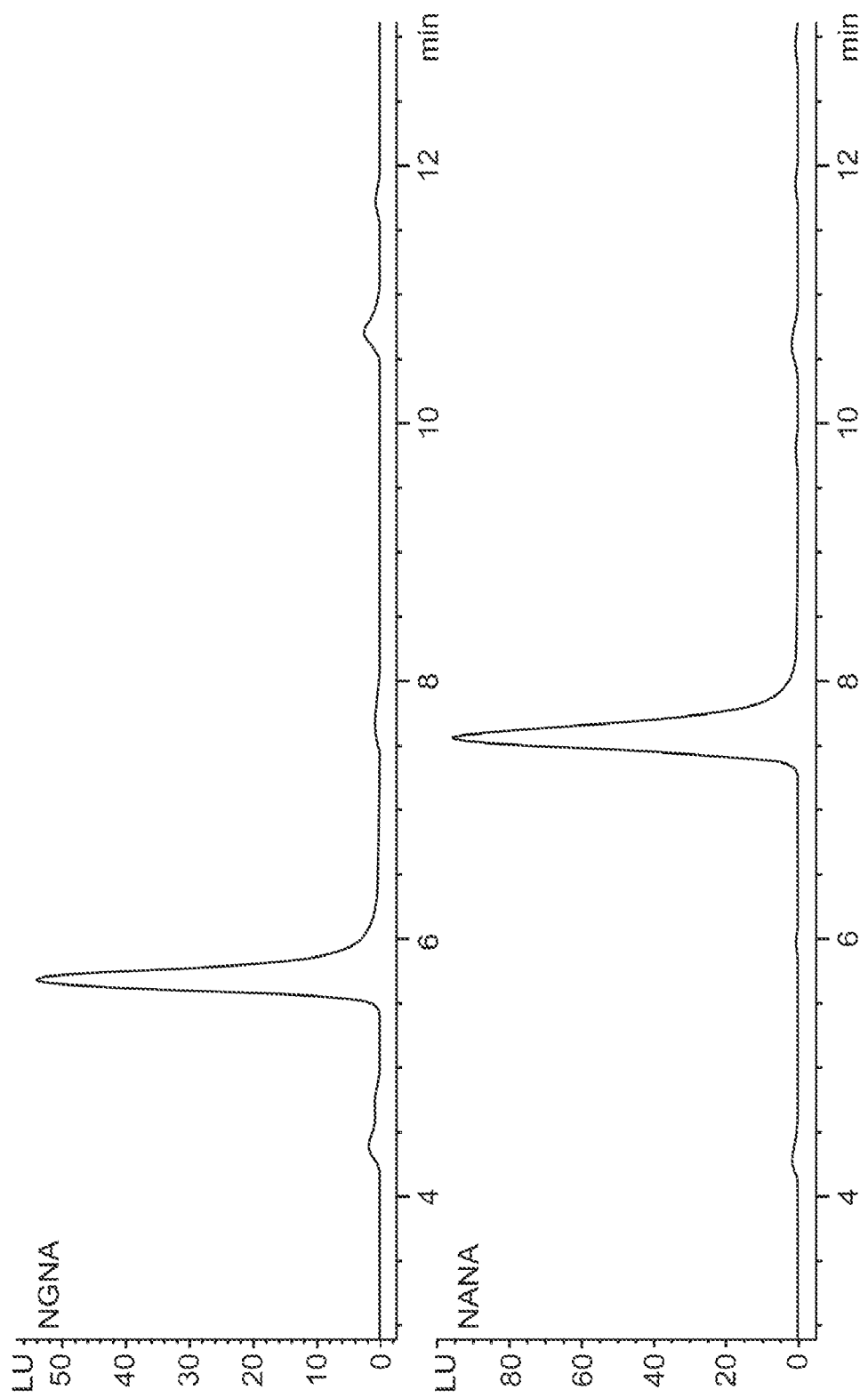
FIG. 14A-B are charts showing LR004 and Erbitux® sialic acid modifications determined by RP-HPLC.
Figure 14B:
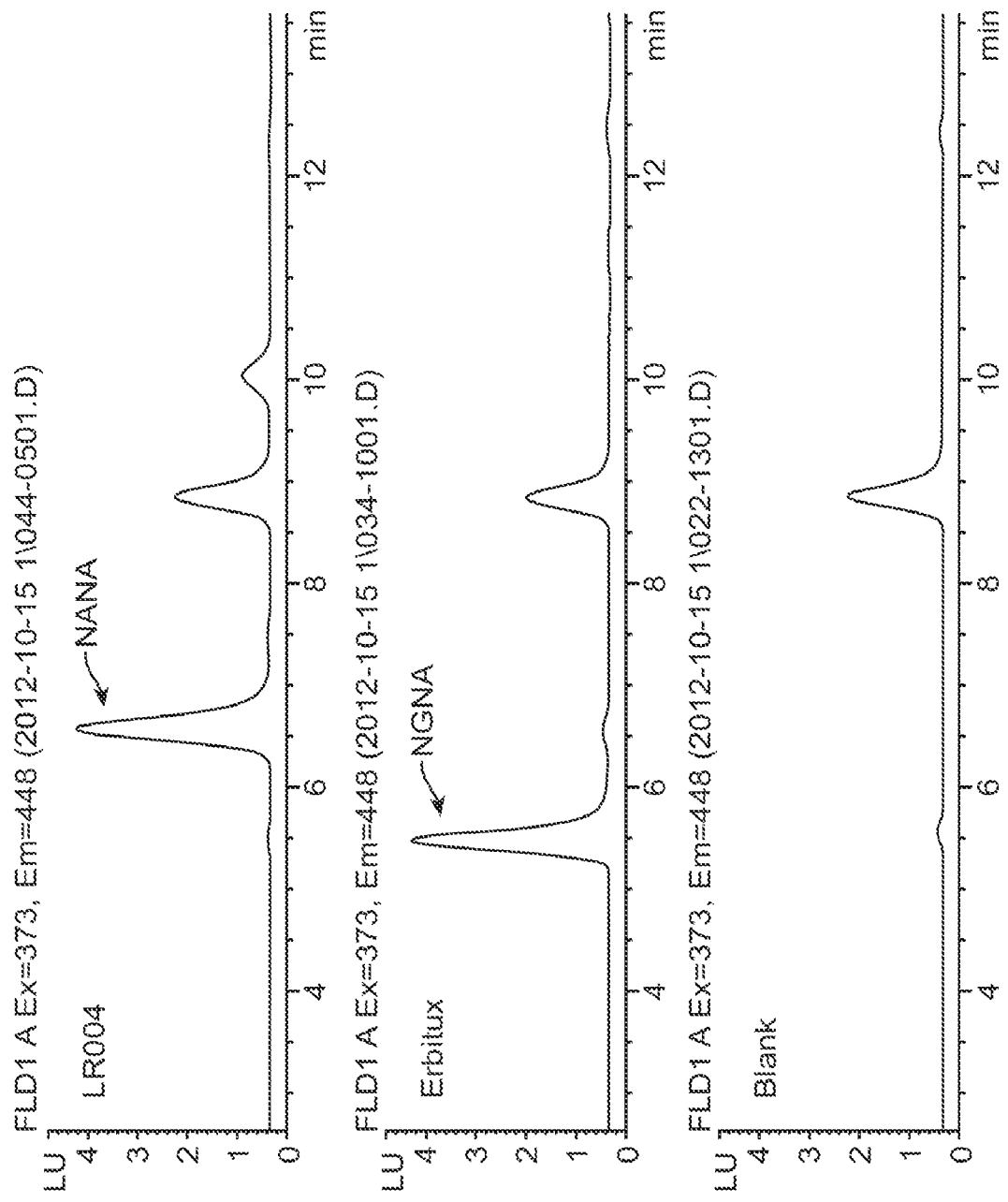

Results are shown in FIG. 14. FIG. 14A shows NGNA and NANA standard peaks migrating at less than 6 and greater than 6 minutes, respectively. FIG. 14B shows the migration of LR004-derived sialic acid at greater than 6 minutes, corresponding to NANA. By contrast, Erbitux®-derived sialic acid migrates at less than 6 minutes, corresponding to NGNA.

B. ELISA Detection of Neu5Gc (N-Glycolylneuraminic Acid (NGNA))

Erbitux® and LR004 were diluted to 100 μg/mL and added to microtiter plates at 2.5, 5.5, and 10 μg/well. Plates were coated overnight at 4° C. Wells were washed three times with PBST and blocked with 200 μl of 0.5% PBST at room temperature for 1 hr. Wells were incubated with 1:1000 chicken anti-Neu5Gc IgY or IgY isotype control at room temperature for 2 hrs., washed five times with PBST, and incubated with 1:1000 donkey anti-chicken IgY-Fc-HRP at room temperature for 1 hr. After washing, wells were developed with a TMB substrate and terminated by adding 10% $H_2SO_4$. Absorbance was measured at 450 nm.

TABLE 14

LR004 and Erbitux ® Neu5Gc Levels Determined by ELISA (OD450 nm)

| | Erbitux | | | LR004 | | |
| --- | --- | --- | --- | --- | --- | --- |
| Antibody | 10 μg | 5 μg | 2.5 μg | 10 μg | 5 μg | 2.5 μg |
| Anti-Neu5Gc IgY | 1.538 | 1.460 | 1.376 | 0.442 | 0.398 | 0.426 |
| IgY control | 0.824 | 0.772 | 0.697 | 0.738 | 0.654 | 0.679 |

Figure 15:
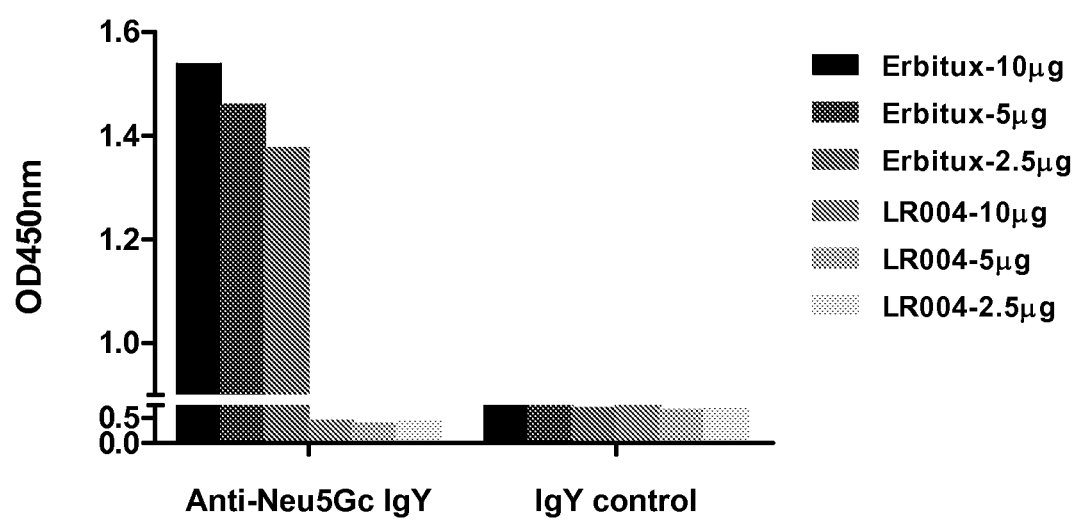
FIG. 15 is a charts showing LR004 and Erbitux® Neu5Gc (N-glycolylneuraminic acid (NGNA)) levels determined by ELISA.

Results are shown in Table 14 and FIG. 15. Erbitux® samples showed Neu5Gc levels 1.87-1.97 fold that of negative controls. By contrast, LR004 showed Neu5Gc levels comparable to negative controls.

Example 9: Thermostability of LR004

The thermostability of LR004 was determined by differential scanning calorimetry (DSC). LR004 and Erbitux® were prepared in formulation buffer (100 mM NaCl, 100 mM Glycine, 0.01% polysorbate 80, 10 mM citric acid, pH 5.5) at a concentration of 5 mg/ml. DSC was performed on a SII Seiko-DSC using standard protocols. All samples were degassed for 5 minutes before analysis. The reference cell was filled with the formulation buffer. Sample were heated from 4° C. to 100° C. at a rate of 60° C./hr.

Figure 16A:
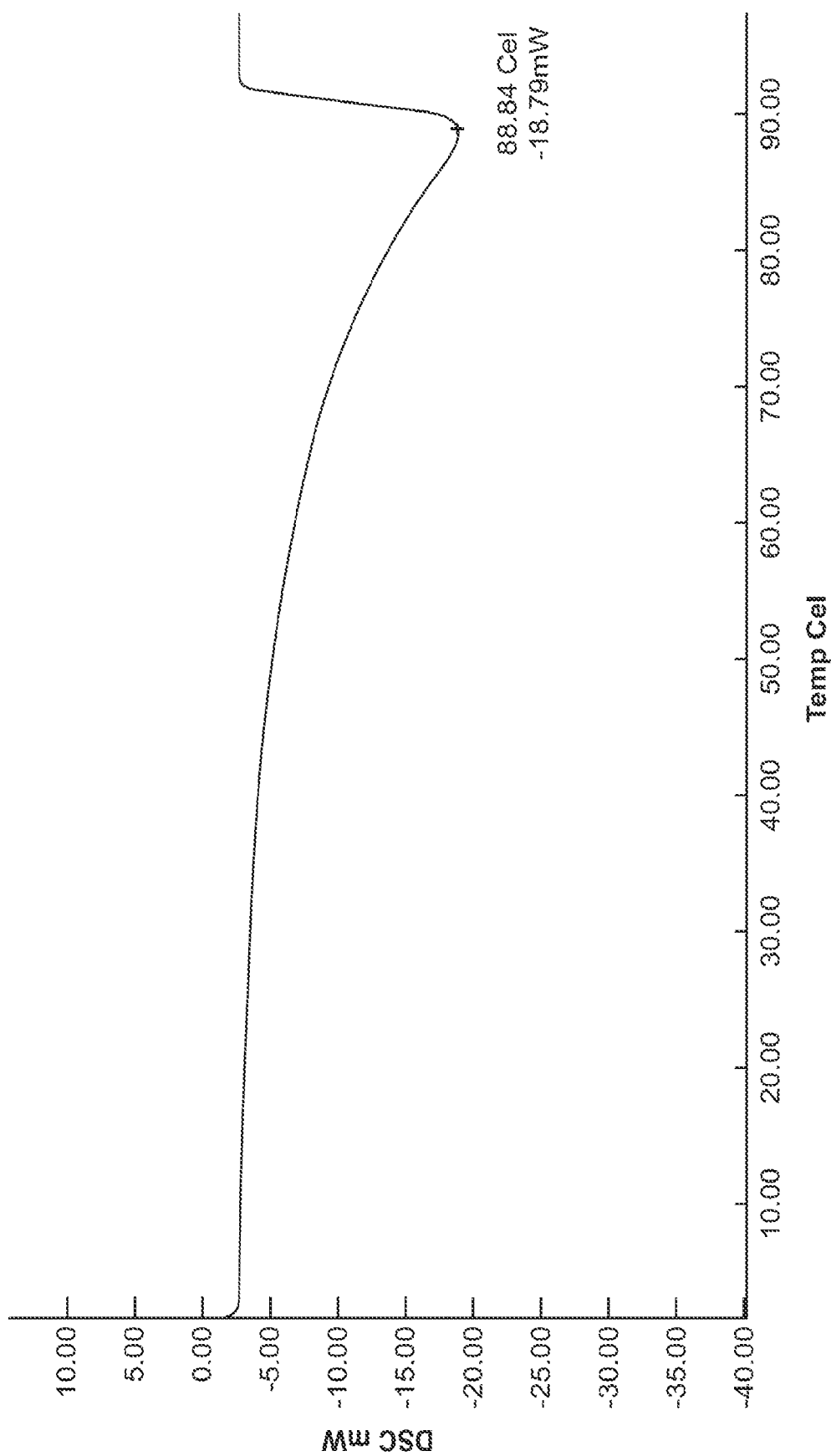
FIG. 16A-B are charts showing the thermostability of LR004 and Erbitux® determined by differential scanning calorimetry (DSC).
Figure 16B:
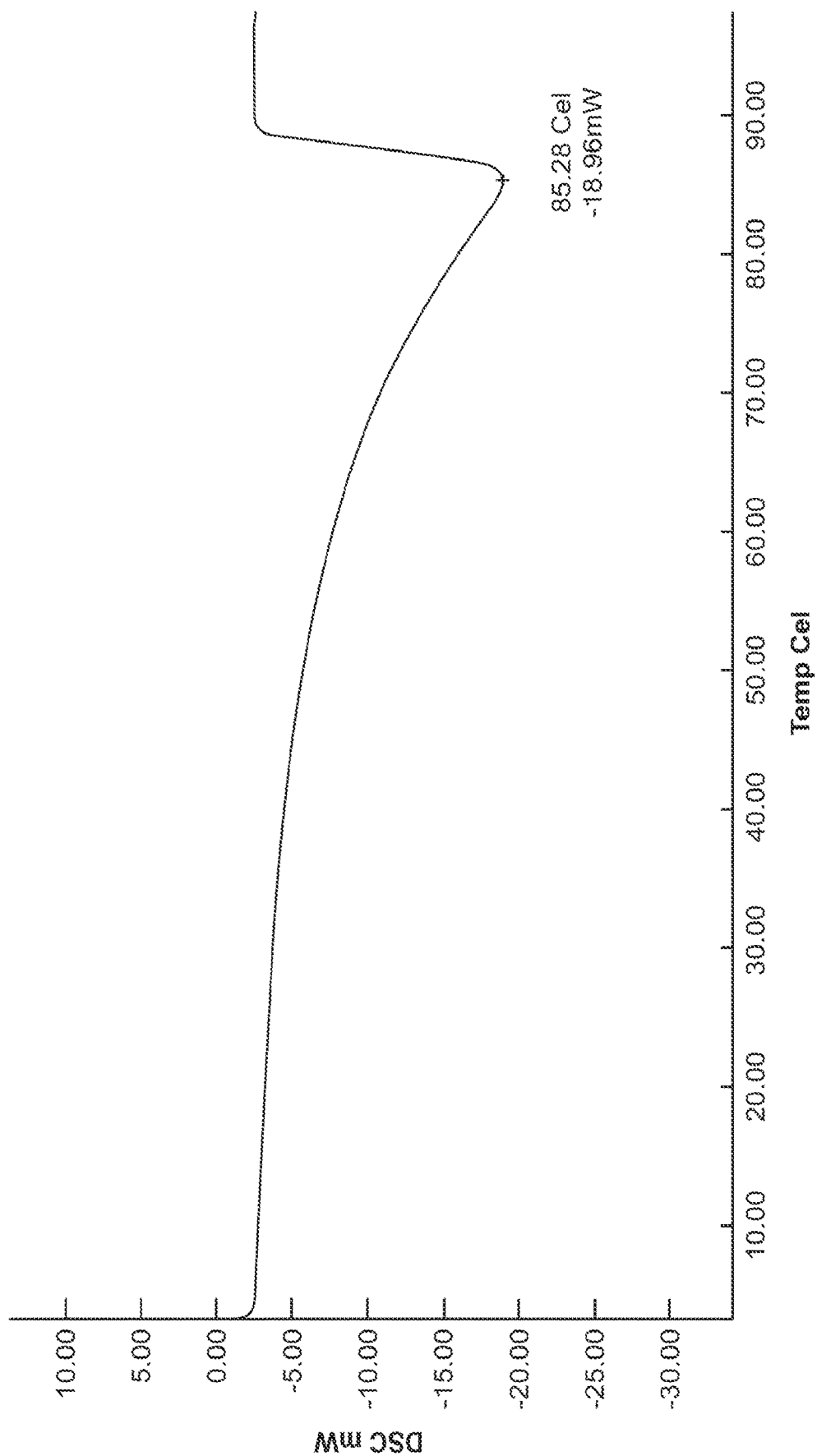

Results are shown in FIG. 16. FIG. 16A shows LR004 to have a melting point of 88.84° C. FIG. 16B shows Erbitux® to have a melting point of 85.28° C. Accordingly, LR004 is has a higher degree of thermostability than Erbutix®.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

The invention claimed is:

1. An antibody which binds epidermal growth factor receptor (EGFR) comprising a heavy chain consisting of the amino acid sequence set forth in SEQ ID NO:2 in combination with a light chain consisting of the amino acid sequence set forth in SEQ ID NO:1, wherein the antibody comprises N-acetylneuraminic acid (NANA) and lacks galactose-α-1,3-galactose, wherein the antibody comprises disulfide bonds between amino acid residues:
   Cys23 and Cys88 of SEQ ID NO:1;
   Cys134 and Cys184 of SEQ ID NO:1;
   Cys214 of SEQ ID NO: 1 and Cys225 of SEQ ID NO: 2;
   Cys22 and Cys95 of SEQ ID NO:2;
   Cys146 and Cys202 of SEQ ID NO:2;
   Cys266 and Cys326 of SEQ ID NO:2; and
   Cys372 and Cys430 of SEQ ID NO:2;
   wherein SEQ ID NO: 2 comprises N-glycan at amino acid residues Asn88 and Asn302; and
   wherein the N-glycan at amino acid residue Asn88 comprises NANA.

2. The antibody of claim 1, wherein the antibody is conjugated to a detectable marker.

3. The antibody of claim 2, wherein the detectable marker comprises a radionuclide or a fluorescent label.

4. The antibody of claim 1, wherein the antibody is conjugated to one or more additional therapeutic agents.

5. The antibody of claim 4, wherein:
   a) the additional therapeutic agent is selected from the group consisting of a *vinca* alkaloid, a microtubule disrupting agent, an anti-angiogenic agent, and a therapeutic antibody; or wherein
   b) the additional therapeutic agent is selected from the group consisting of an EGFR targeting agent, a tyrosine kinase targeting agent, a transitional metal complex, a proteasome inhibitor an antimetabolite, an alkylating agent, a platinum-based agent, an anthracycline antibiotic, a topoisomerase inhibitor, a macrolide, and a retinoid; or wherein
   c) the additional therapeutic agent is selected from the group consisting of geldanamycin or a derivative thereof, adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof, topetecan, vinblastine, vincristine, tamoxifen, piposulfan, nab-5404, nab-5800, and nab-5801; or wherein
   d) the additional therapeutic agent is selected from the group consisting Irinotecan, HKP, Ortataxel, gemcitabine, Oxaliplatin, Herceptin®, vinorelbine, Doxil®, capecitabine, Alimta®, Avastin®, Velcade®, Tarceva®, Neulasta®, lapatinib, and sorafenib.

6. A composition comprising the antibody of claim 1, wherein the antibody has a higher degree of thermostability than Erbutix® (cetuximab), and wherein the antibody does not induce a hypersensitivity response in a subject hypersensitive to cetuximab or predisposed to having a hypersensitivity reaction to cetuximab.

7. The composition of claim 6, further comprising a chemotherapeutic agent, wherein:
   a) the chemotherapeutic agent is selected from the group consisting of a vinca alkaloid, a microtubule disrupting agent, an anti-angiogenic agent, and a therapeutic antibody; or wherein
   b) the chemotherapeutic agent is selected from the group consisting of an EGFR targeting agent, a tyrosine kinase targeting agent, a transitional metal complex, a proteasome inhibitor, an antimetabolite, an alkylating agent, a platinum-based agent, an anthracycline antibiotic, a topoisomerase inhibitor, a macrolide, and a retinoid; or wherein
   c) the chemotherapeutic agent is selected from the group consisting of geldanamycin or a derivative thereof, adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof, topetecan, vinblastine, vincristine, tamoxifen, piposulfan, nab-5404, nab-5800, and nab-5801; or wherein
   d) the chemotherapeutic agent is selected from the group consisting of Irinotecan, HKP, Ortataxel, gemcitabine, Oxaliplatin, Herceptin®, vinorelbine, Doxil®, capecitabine, Alimta®, Avastin®, Velcade®, Tarceva®, Neulasta®, lapatinib, and sorafenib.

8. The antibody of claim 1, wherein the antibody has a higher degree of thermostability than Erbutix® (cetuximab), and wherein the antibody does not induce a hypersensitivity response in a subject hypersensitive to cetuximab or predisposed to having a hypersensitivity reaction to cetuximab.

9. A Chinese hamster ovary (CHO) cell comprising polynucleotides encoding the antibody of claim 1.

10. The CHO cell of claim 9, wherein the nucleic acids are present on a replicable vector separate from the CHO cell genome.

11. The CHO cell of claim 9, wherein the nucleic acids are stably integrated into the CHO cell genome.

12. A method of producing the antibody of claim 1, comprising introducing into a Chinese hamster ovary (CHO) cell with polynucleotides encoding the amino acid sequences set forth in SEQ ID NO: 1 and SEQ ID NO: 2, wherein the CHO cell subsequently expresses the nucleic acid sequences and produces an antibody comprising a heavy chain consisting of the amino acid sequence set forth in SEQ ID NO: 1 in combination with a light chain consisting of the amino acid sequence set forth in SEQ ID NO: 2.

13. A method for treating an EGFR-expressing cancer in a subject in need thereof, comprising administering to the subject the antibody of claim 1, and further comprising determining whether the subject is hypersensitive to cetuximab or is predisposed to having a hypersensitivity reaction to cetuximab, wherein the antibody has a higher degree of thermostability than Erbutix® (cetuximab).

14. The method of claim 13, further comprising administering one or more additional therapeutic agents, wherein:
a) the additional therapeutic agent is selected from the group consisting of a vinca alkaloid, a microtubule disrupting agent, an anti-angiogenic agent, and a therapeutic antibody; or wherein
b) the additional therapeutic agent is selected from the group consisting of an EGFR targeting agent, a tyrosine kinase targeting agent, a transitional metal complex, a proteasome inhibitor, an antimetabolite, an alkylating agent, a platinum-based agent, an anthracycline antibiotic, a topoisomerase inhibitor, a macrolide, and a retinoid; or wherein
c) the additional therapeutic agent is selected from the group consisting of geldanamycin or a derivative thereof, adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl-CCNU, cisplatin, etoposide, interferons, camptothecin and derivatives thereof, phenesterine, taxanes and derivatives thereof, topetecan, vinblastine, vincristine, tamoxifen, piposulfan, nab-5404, nab-5800, and nab-5801; or wherein
d) the additional therapeutic agent is selected from the group consisting of Irinotecan, HKP, Ortataxel, gemcitabine, Oxaliplatin, Herceptin®, vinorelbine, Doxil®, capecitabine, Alimta®, Avastin®, Velcade®, Tarceva®, Neulasta®, lapatinib, and sorafenib.

15. The method of claim 13, wherein the antibody is conjugated to one or more additional therapeutic agents.

16. The method of claim 13, wherein the subject has elevated levels of anti-cetuximab IgE compared to a negative control sample.

17. The method of claim 13, wherein the subject has elevated levels of anti-galactose-α-1,3-galactose IgE compared to a negative control sample.

18. The method of claim 13, wherein determining comprises measuring the presence of anti-cetuximab or anti-galactose-α-1,3-galactose IgE in a sample of serum from the subject, wherein an elevated level of anti-cetuximab or anti-galactose-α-1,3-galactose IgE compared to a negative control sample indicates that the subject is hypersensitive to cetuximab or is predisposed to having a hypersensitivity reaction to cetuximab.

* * * * *